United States Patent
Siqueira et al.

(10) Patent No.: US 11,220,085 B2
(45) Date of Patent: Jan. 11, 2022

(54) APERTURED ELASTIC FILM LAMINATES

(71) Applicant: Kimberly-Clark Worldwide, Inc., Neenah, WI (US)

(72) Inventors: Jose Augusto Vidal De Siqueira, Roswell, GA (US); Michael R. Vaughan, Atlanta, GA (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 15 days.

(21) Appl. No.: 16/642,466

(22) PCT Filed: Feb. 28, 2018

(86) PCT No.: PCT/US2018/020321
§ 371 (c)(1),
(2) Date: Feb. 27, 2020

(87) PCT Pub. No.: WO2019/045771
PCT Pub. Date: Mar. 7, 2019

(65) Prior Publication Data
US 2020/0254715 A1    Aug. 13, 2020

Related U.S. Application Data

(60) Provisional application No. 62/552,928, filed on Aug. 31, 2017.

(51) Int. Cl.
*B32B 3/24* (2006.01)
*B32B 3/30* (2006.01)
(Continued)

(52) U.S. Cl.
CPC ........ *B32B 3/266* (2013.01); *A61F 13/15203* (2013.01); *A61F 13/4902* (2013.01);
(Continued)

(58) Field of Classification Search
None
See application file for complete search history.

(56) References Cited

U.S. PATENT DOCUMENTS

| 4,834,741 | A | | 5/1989 | Sabee |
| 4,863,779 | A | * | 9/1989 | Daponte .................. B32B 7/14 |
| | | | | 428/152 |

(Continued)

FOREIGN PATENT DOCUMENTS

| CN | 101522540 A | 9/2009 |
| CN | 201686246 U | 12/2010 |

(Continued)

OTHER PUBLICATIONS

Chang-Hung, Ph.D., Kuo, "On the mechanics of contact and fracture analysis of multi-layered composites", Northwestern University, 1992.

(Continued)

*Primary Examiner* — Jeffrey A Vonch

(57) ABSTRACT

An elastic laminate is provided including at least one gathered outer facing layer of a fabric and an apertured elastic film attached thereto. The aperture film includes a series of alternating first and second segments that extend continuously along the direction of elasticity. The first segments of the film are substantially devoid of any apertures and the second segments are strewn with apertures of irregular size and shape. The regionally limited and irregular apertures are formed by the controlled rupturing of the film within those segments. The elastic laminate has excellent air-permeability and elastic properties.

20 Claims, 10 Drawing Sheets

(51) Int. Cl.
| | |
|---|---|
| *B32B 5/02* | (2006.01) |
| *B32B 7/04* | (2019.01) |
| *B32B 25/10* | (2006.01) |
| *B32B 27/02* | (2006.01) |
| *B32B 27/12* | (2006.01) |
| *B32B 3/26* | (2006.01) |
| *B32B 3/10* | (2006.01) |
| *B32B 7/12* | (2006.01) |
| *B32B 27/32* | (2006.01) |
| *A61F 13/15* | (2006.01) |
| *A61F 13/49* | (2006.01) |
| *B32B 7/05* | (2019.01) |
| *B32B 7/022* | (2019.01) |
| *B32B 25/08* | (2006.01) |
| *A61L 15/24* | (2006.01) |
| *B32B 38/00* | (2006.01) |
| *B32B 27/08* | (2006.01) |
| *B32B 27/30* | (2006.01) |
| *B32B 25/14* | (2006.01) |
| *B32B 37/14* | (2006.01) |
| *B32B 5/14* | (2006.01) |
| *B32B 37/04* | (2006.01) |
| *B32B 37/00* | (2006.01) |

(52) U.S. Cl.
CPC .......... *A61F 13/49019* (2013.01); *B32B 3/10* (2013.01); *B32B 3/26* (2013.01); *B32B 3/30* (2013.01); *B32B 5/022* (2013.01); *B32B 7/022* (2019.01); *B32B 7/05* (2019.01); *B32B 7/12* (2013.01); *B32B 25/08* (2013.01); *B32B 25/10* (2013.01); *B32B 27/02* (2013.01); *B32B 27/12* (2013.01); *B32B 27/32* (2013.01); *A61F 2013/15406* (2013.01); *A61F 2013/15552* (2013.01); *A61F 2013/49023* (2013.01); *A61F 2013/49025* (2013.01); *A61F 2013/49093* (2013.01); *A61L 15/24* (2013.01); *B32B 5/02* (2013.01); *B32B 5/142* (2013.01); *B32B 5/147* (2013.01); *B32B 7/04* (2013.01); *B32B 25/14* (2013.01); *B32B 27/08* (2013.01); *B32B 27/302* (2013.01); *B32B 37/0076* (2013.01); *B32B 37/04* (2013.01); *B32B 37/14* (2013.01); *B32B 2037/0092* (2013.01); *B32B 2038/0028* (2013.01); *B32B 2250/02* (2013.01); *B32B 2250/03* (2013.01); *B32B 2250/242* (2013.01); *B32B 2250/246* (2013.01); *B32B 2250/40* (2013.01); *B32B 2262/0253* (2013.01); *B32B 2274/00* (2013.01); *B32B 2307/51* (2013.01); *B32B 2307/54* (2013.01); *B32B 2307/718* (2013.01); *B32B 2307/724* (2013.01); *B32B 2307/726* (2013.01); *B32B 2307/7265* (2013.01); *B32B 2323/04* (2013.01); *B32B 2323/10* (2013.01); *B32B 2325/00* (2013.01); *B32B 2555/02* (2013.01); *Y10T 428/2457* (2015.01); *Y10T 428/24298* (2015.01); *Y10T 428/24322* (2015.01); *Y10T 428/24331* (2015.01); *Y10T 428/24446* (2015.01); *Y10T 428/24942* (2015.01); *Y10T 428/24992* (2015.01); *Y10T 428/27* (2015.01); *Y10T 442/659* (2015.04); *Y10T 442/678* (2015.04); *Y10T 442/679* (2015.04)

(56) References Cited

U.S. PATENT DOCUMENTS

| | | | | |
|---|---|---|---|---|
| 4,883,549 | A | * | 11/1989 | Frost ................. A61F 13/15593 156/161 |
| 4,908,251 | A | * | 3/1990 | Iimura .................... B32B 7/12 428/68 |
| 5,167,897 | A | * | 12/1992 | Weber ............... A61F 13/15593 264/288.8 |
| 5,370,764 | A | * | 12/1994 | Alikhan ............ A61F 13/53717 156/553 |
| 5,501,679 | A | * | 3/1996 | Krueger ................. B32B 25/08 604/393 |
| 5,580,418 | A | * | 12/1996 | Alikhan ............... A61F 13/5116 156/553 |
| 5,683,787 | A | * | 11/1997 | Boich ...................... B32B 7/12 428/198 |
| 5,691,034 | A | * | 11/1997 | Krueger ................. B29C 59/00 428/152 |
| 5,769,993 | A | * | 6/1998 | Baldauf ................. B32B 5/022 156/164 |
| 5,770,144 | A | * | 6/1998 | James ............... A61F 13/15731 264/504 |
| 5,804,021 | A | | 9/1998 | Abuto et al. |
| 5,851,935 | A | * | 12/1998 | Srinivasan ............. B32B 5/022 442/328 |
| 5,861,074 | A | * | 1/1999 | Wu ........................ B32B 27/04 156/229 |
| 5,914,084 | A | | 6/1999 | Benson et al. |
| 5,932,497 | A | * | 8/1999 | Morman ............. A61F 13/5148 442/286 |
| 5,952,252 | A | * | 9/1999 | Shawver ................ D04H 1/559 442/407 |
| 5,997,986 | A | * | 12/1999 | Turi ................... A61F 13/15731 428/138 |
| 6,057,024 | A | | 5/2000 | Mleziva et al. |
| 6,069,097 | A | * | 5/2000 | Suzuki ............... A61F 13/49009 442/328 |
| 6,245,401 | B1 | * | 6/2001 | Ying ................... A61F 13/5146 428/58 |
| 6,277,479 | B1 | * | 8/2001 | Campbell ......... A61F 13/51462 428/213 |
| 6,313,372 | B1 | * | 11/2001 | Suzuki ................ A61F 13/4902 156/183 |
| 6,368,444 | B1 | | 4/2002 | Jameson et al. |
| 6,403,505 | B1 | * | 6/2002 | Groitzsch .............. D04H 13/00 442/394 |
| 6,537,930 | B1 | * | 3/2003 | Middlesworth ........... B32B 7/04 442/39 |
| 6,605,172 | B1 | * | 8/2003 | Anderson ............... B29C 55/18 156/199 |
| 6,620,485 | B1 | | 9/2003 | Benson et al. |
| 6,855,424 | B1 | * | 2/2005 | Thomas ............. A61F 13/4902 264/51 |
| 6,884,494 | B1 | | 4/2005 | Curro et al. |
| 6,982,231 | B1 | * | 1/2006 | Uitenbroek ............... B32B 5/26 442/394 |
| 7,351,297 | B2 | | 4/2008 | Middlesworth et al. |
| 7,470,340 | B2 | | 12/2008 | Baldauf et al. |
| 7,507,680 | B2 | | 3/2009 | Middlesworth et al. |
| 7,803,244 | B2 | | 9/2010 | Siqueira et al. |
| 8,012,388 | B2 | | 9/2011 | Akaki et al. |
| 8,067,063 | B2 | | 11/2011 | Desai et al. |
| 8,187,243 | B2 | | 5/2012 | Mansfield et al. |
| 8,241,543 | B2 | | 8/2012 | Hugh |
| 8,292,865 | B2 | | 10/2012 | Hutson et al. |
| 8,603,281 | B2 | | 12/2013 | Welch et al. |
| 8,945,452 | B2 | | 2/2015 | Morita et al. |
| 9,067,396 | B2 | | 6/2015 | Ishikawa et al. |
| 9,314,991 | B2 | | 4/2016 | Ceusters et al. |
| 2002/0016122 | A1 | * | 2/2002 | Curro ................... B32B 37/144 442/381 |
| 2002/0022426 | A1 | * | 2/2002 | Curro ................... B29C 66/436 442/373 |

(56) References Cited

U.S. PATENT DOCUMENTS

| | | | |
|---|---|---|---|
| 2002/0065009 A1* | 5/2002 | Pelkie | B32B 3/30 442/182 |
| 2002/0074691 A1* | 6/2002 | Mortellite | B29C 48/08 264/288.4 |
| 2002/0089087 A1* | 7/2002 | Mushaben | B32B 3/28 264/288.4 |
| 2002/0164465 A1* | 11/2002 | Curro | B29C 65/18 428/198 |
| 2003/0059587 A1* | 3/2003 | Grimm | D04H 1/5412 428/196 |
| 2003/0105446 A1* | 6/2003 | Hutson | B32B 7/02 604/385.22 |
| 2003/0181120 A1* | 9/2003 | Wu | A41D 31/145 442/394 |
| 2003/0213549 A1* | 11/2003 | McAmish | B32B 38/0032 156/229 |
| 2004/0161586 A1* | 8/2004 | Cree | B32B 37/153 428/131 |
| 2004/0222553 A1* | 11/2004 | Desai | B29C 55/026 264/171.24 |
| 2005/0003152 A1* | 1/2005 | Thomas | B32B 3/266 428/131 |
| 2005/0101216 A1* | 5/2005 | Middlesworth | B32B 5/04 442/394 |
| 2005/0106980 A1* | 5/2005 | Abed | B32B 5/022 442/395 |
| 2005/0249915 A1* | 11/2005 | Wood | A61F 13/15593 428/131 |
| 2006/0003656 A1 | 1/2006 | Morman | |
| 2006/0063454 A1 | 3/2006 | Chung et al. | |
| 2006/0131783 A1* | 6/2006 | Morman | B29C 55/12 264/290.2 |
| 2006/0148361 A1* | 7/2006 | Ng | B29C 55/18 442/394 |
| 2007/0105472 A1* | 5/2007 | Marche | D04H 13/00 442/394 |
| 2007/0144660 A1* | 6/2007 | O'Sickey | B29C 65/028 156/229 |
| 2007/0287348 A1* | 12/2007 | Autran | A61F 13/51478 442/327 |
| 2008/0095978 A1* | 4/2008 | Siqueira | B32B 37/24 428/137 |
| 2008/0128077 A1 | 6/2008 | Baldauf et al. | |
| 2008/0228159 A1* | 9/2008 | Anderson | A61F 13/51478 604/378 |
| 2009/0191779 A1* | 7/2009 | Cree | B29C 65/02 442/361 |
| 2009/0208703 A1* | 8/2009 | Wennerback | B32B 27/12 428/138 |
| 2009/0264844 A1* | 10/2009 | Autran | C08L 23/142 604/365 |
| 2009/0306616 A1* | 12/2009 | Wennerback | A61F 13/15203 604/367 |
| 2010/0022151 A1* | 1/2010 | Malowaniec | B32B 5/04 442/329 |
| 2010/0076390 A1* | 3/2010 | Norrby | B29C 55/023 604/367 |
| 2010/0145295 A1* | 6/2010 | Isele | A61F 13/51484 604/365 |
| 2010/0297387 A1* | 11/2010 | Rasmussen | B32B 37/0053 428/114 |
| 2011/0160691 A1* | 6/2011 | Ng | B32B 27/12 604/385.23 |
| 2011/0282313 A1 | 11/2011 | Lu et al. | |
| 2012/0003421 A1* | 1/2012 | Sollmann | B32B 37/18 428/131 |
| 2012/0064271 A1 | 3/2012 | Broering et al. | |
| 2012/0094819 A1* | 4/2012 | Azuma | B29C 55/18 493/339 |
| 2012/0168063 A1* | 7/2012 | Beuther | A61F 13/15699 156/163 |
| 2012/0238981 A1 | 9/2012 | Weisman et al. | |
| 2012/0251771 A1 | 10/2012 | Wilson et al. | |
| 2013/0000819 A1 | 1/2013 | Hutson et al. | |
| 2013/0048204 A1* | 2/2013 | Chang | C09D 153/025 156/244.11 |
| 2014/0073211 A1 | 3/2014 | Bruce | |
| 2014/0093703 A1* | 4/2014 | Hanschen | B32B 25/10 428/175 |
| 2014/0093716 A1* | 4/2014 | Hanschen | B32B 7/12 428/221 |
| 2014/0130956 A1* | 5/2014 | Floberg | B32B 37/144 156/73.5 |
| 2014/0220328 A1* | 8/2014 | Ausen | B29C 48/05 428/219 |
| 2014/0234605 A1* | 8/2014 | Ausen | B29C 48/11 428/219 |
| 2014/0234606 A1* | 8/2014 | Ausen | B29C 48/21 428/220 |
| 2014/0248471 A1* | 9/2014 | Hanschen | B32B 5/145 428/189 |
| 2014/0302286 A1* | 10/2014 | Okuda | B32B 3/28 428/184 |
| 2014/0329053 A1* | 11/2014 | Baldauf | D04H 1/593 428/152 |
| 2014/0349079 A1 | 11/2014 | Chandrasekaran et al. | |
| 2015/0079337 A1* | 3/2015 | Ausen | B29C 43/24 428/136 |
| 2015/0164705 A1 | 6/2015 | Thomas et al. | |
| 2015/0273802 A1* | 10/2015 | Lee | B32B 25/14 428/483 |
| 2016/0159534 A1 | 6/2016 | Ujiie | |
| 2016/0184144 A1* | 6/2016 | Mansfield | A61F 13/58 604/385.04 |
| 2016/0362824 A1* | 12/2016 | Ausen | A61F 13/0273 |
| 2017/0000660 A1 | 1/2017 | Wade et al. | |
| 2017/0087029 A1* | 3/2017 | Nelson | B32B 7/02 |
| 2017/0096265 A1 | 4/2017 | Kieffer et al. | |
| 2017/0189244 A1* | 7/2017 | Mueller | A61F 13/4902 |
| 2017/0290717 A1 | 10/2017 | Schoenbeck et al. | |
| 2017/0296399 A1* | 10/2017 | Kline | B32B 27/302 |
| 2017/0326832 A1* | 11/2017 | Palzewicz | B32B 25/14 |
| 2018/0014984 A1 | 1/2018 | Sakai | |
| 2018/0015709 A1* | 1/2018 | Takeuchi | A61F 13/496 |
| 2018/0028371 A1* | 2/2018 | Takaishi | A61F 13/514 |
| 2018/0256414 A1* | 9/2018 | Maschino | B32B 25/14 |

FOREIGN PATENT DOCUMENTS

| | | | | |
|---|---|---|---|---|
| CN | 102302400 B | | 5/2014 | |
| DE | 19647459 A1 | * | 5/1998 | ......... B32B 37/0084 |
| DE | 10061894 A1 | * | 7/2001 | ............... B32B 3/30 |
| EP | 0217032 B1 | | 2/1992 | |
| EP | 0820747 A1 | * | 1/1998 | ......... A61F 13/4902 |
| EP | 0700672 B1 | | 5/2000 | |
| EP | 2096201 B1 | | 6/2015 | |
| EP | 1397101 B1 | | 2/2016 | |
| EP | 2990018 A1 | | 3/2016 | |
| JP | 08300531 A | * | 11/1996 | ........... D04H 1/4358 |
| JP | 2011079255 A | * | 4/2011 | |
| JP | 2016055481 A | * | 4/2016 | |
| JP | 5967736 B1 | | 8/2016 | |
| KR | 20050047009 A | * | 5/2005 | ............... B32B 5/26 |
| WO | 9609428 A1 | | 3/1996 | |
| WO | 9937841 A1 | | 7/1999 | |
| WO | WO-9932698 A1 | * | 7/1999 | ........... D04H 1/4358 |
| WO | WO-2009111303 A1 | * | 9/2009 | ............... B32B 5/26 |
| WO | WO-2012036599 A1 | * | 3/2012 | ......... A61F 13/4902 |

OTHER PUBLICATIONS

Co-Pending U.S. Appl. No. 16/642,480, filed Feb. 27, 2020, by Siqueira et al. for "Composite Elastic Laminate Having Discrete Film Segments."

(56) References Cited

OTHER PUBLICATIONS

Co-Pending U.S. Appl. No. 16/642,528, filed Feb. 27, 2020, by Siqueira et al. for "Composite Elastic Laminate Having Discrete Film Segments."

* cited by examiner

APERTURED ELASTIC FILM LAMINATES

BACKGROUND

Elastic materials are commonly incorporated into clothing and personal care articles worn on or about the body in order to improve fit and the ability of the article to conform to the contours of a moving body. Examples of such articles include diapers, training pants, adult incontinence garments, personal protective garments, bandages, and so forth. However, elastic materials often present an undesirable hand-feel such as having a tacky or rubbery feel. Thus, in clothing and personal care articles, it is common to employ elastic materials between one or more outer facing materials that present a pleasing hand. For example, in personal care articles it is common to have one or more nonwoven fabrics with the desired hand-feel laminated to the elastic material as an outer facing so that the elastic laminate is more pleasing to the touch. In one practice, the nonwoven fabric is joined to an elastic film while the film is in a stretched condition so that, upon retraction of the elastic film, the nonwoven fabric bunches and forms gathers between the locations where it is bonded to the elastic film. The resulting elastic laminate is stretchable at least to the extent that the nonwoven fabric can extend by flattening out the gathers located between the bond sites. Examples of such stretch bonded elastic laminates are disclosed in numerous references including, for example, in U.S. Pat. No. 4,720,415 to Vander Wielen et al. and U.S. Pat. No. 5,385,775 to Wright et al.

In order to support skin wellness, there is also a desire that such elastic laminates allow water vapor, trapped between the skin of the wearer and the laminate, to escape. These are commonly referred to as 'breathable' materials. Most elastomeric polymer films have very low water vapor transmission rates and would not be considered to be breathable. Thus, it has become common to perforate such elastic laminates in order to allow water vapor trapped against the skin to escape. Examples of such apertured elastic laminates include those described in U.S. Pat. No. 7,803,244 Siqueira et al., U.S. Pat. No. 8,241,542 O'Donnell et al., U.S. Pat. No. 8,292,865 to Hutson et al. and EP1397101B1 Curro et al.

However, many aperturing techniques can degrade the elastic properties of the film and corresponding laminate. Therefore, a need remains for methods of efficiently making elastic laminates at high production speeds that are sufficiently breathable to support skin-wellness, and that more effectively utilize the contractive power of the elastic material employed in the laminate.

SUMMARY

The present invention provides a multilayer elastic laminate that is elastic in at least a first direction and that includes an elastic film and at least one fabric that is extensible in the first direction. The film includes a plurality of interposed first and second segments that extend continuously in the first direction wherein the first segments are substantially devoid of apertures and the second segments are strewn with irregular, randomly positioned apertures. The second segments have apertures of sufficient size and number such that the laminate has an air permeability of between about 150-1000 CFM. In certain embodiments, the first and second segments extend continuously in the first direction and, along a direction perpendicular to the first direction, may each have a frequency of between about 0.5 and 14 segments per cm. Additionally and/or alternatively, the first and second segments extend a length, along the direction perpendicular to the first direction, of between about 2 mm and 20 mm. In still further embodiments, the areas of the laminate corresponding to the second segments of the film may have a lower average basis weight relative to those corresponding to the first segments of the film.

In certain embodiments, the elastic laminate includes at least two fabric layers and the layers can be positioned such that film is located between the two fabric layers. Still further, in certain other embodiments, the one or more fabrics comprise a nonwoven web of olefin polymer fibers. The elastic film may comprise a thermoplastic elastomer such as one selected from the group of olefin elastomers, styrenic block copolymers and blends thereof. In certain embodiments, the elastic film can predominantly comprise an olefin elastomer such as, for example, an ethylene or propylene elastomer.

Further, in still other embodiments, the Vicat softening point of the fibers forming the fabric can be lower than that of the film, such as, for example, being at least about 10° C. lower. In certain embodiments, the film may be bonded to the fibers of one or more of the fabrics such as being directly bonded to the fibers of a nonwoven web.

In still further embodiments, the one or more fabric layers will have gathers spanning or extending across the first and second segments of the elastic film; these gathers allow the laminate to extend as the gathers are pulled flat. In still further embodiments, the elastic laminate may have a basis weight, in an untensioned state, of between about 25 and about 90 g/m². Additionally and/or alternatively, the film may comprise between about 10% and about 40% by weight of the laminate. Further, in certain embodiments, the elastic laminate can have a percent stretch of between about 75% and about 260% at 2000 g-f.

DETAILED DESCRIPTION

Figure 1:
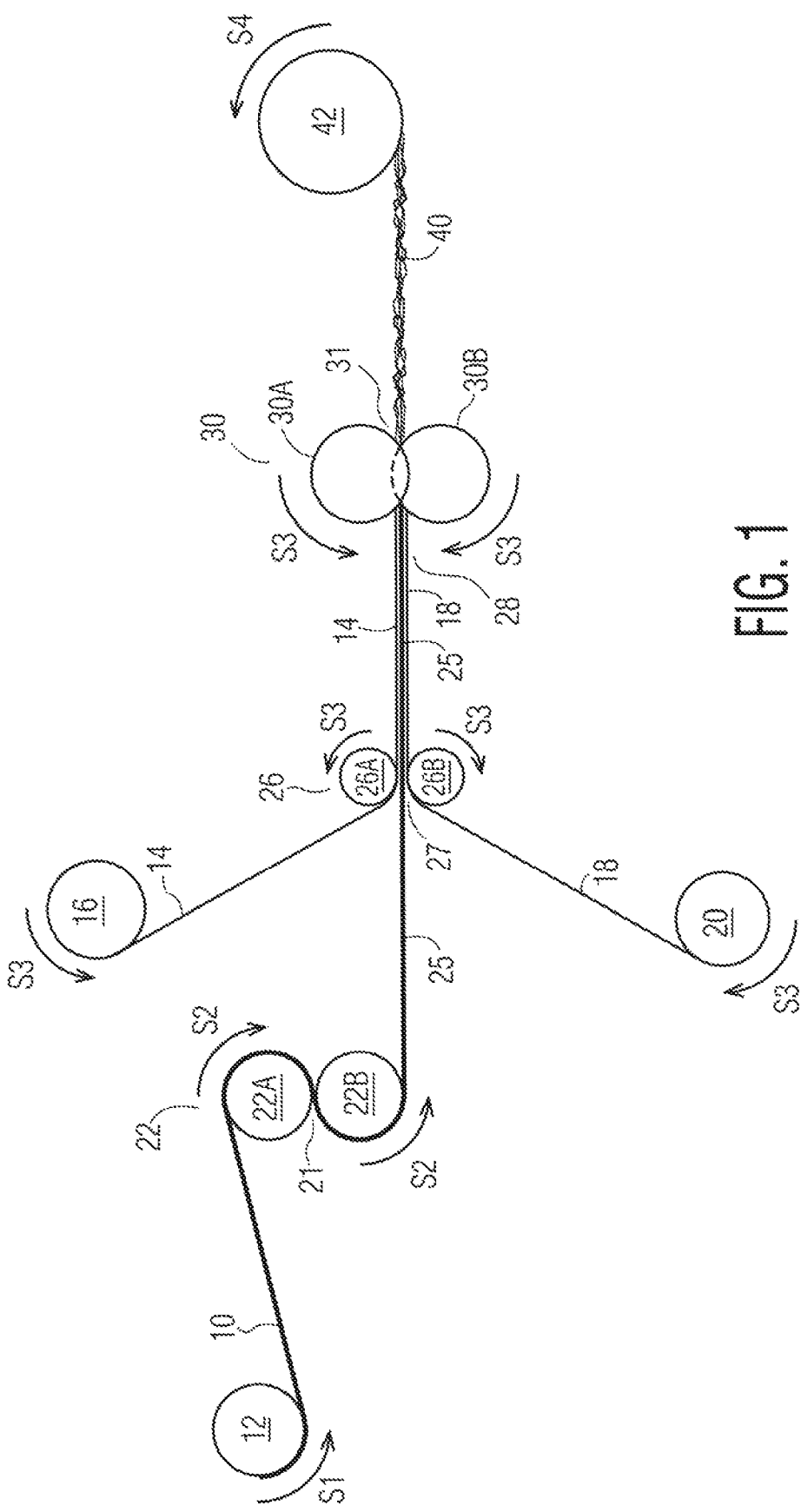
FIG. 1 is a schematic illustration of a method for forming an elastic laminate of the present invention.

Throughout the specification and claims, discussion of the articles and/or individual components thereof is with the understanding set forth below.

The term "comprising" or "including" or "having" are inclusive or open-ended and do not exclude additional unrecited elements, compositional components, or method steps. Accordingly, the terms "comprising" or "including" or "having" encompass the more restrictive terms "consisting essentially of" and "consisting of."

As used herein the term "aperture" means a continuous uninterrupted hole or opening that extends through the entire thickness of a layer, or where the context so implies, through the thickness of the entire laminate.

As used herein, the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

As used herein "propylene polymer" means a polymer having greater than 50% propylene content (mole percent).

As used herein "ethylene polymer" means a polymer having greater than 50% ethylene content (mole percent).

As used herein "olefin polymer" means a polymer having greater than 50% olefin content (mole percent).

As used herein, the term "fabric" means a cohesive fibrous sheet-like material including woven, knitted, and nonwoven materials.

As used herein, the term "nonwoven web" means a structure or a web of material that has been formed without use of traditional fabric forming processes such as weaving or knitting, to produce a structure of individual fibers or threads that are entangled or intermeshed, but not in an identifiable, repeating manner.

As used herein "spunbond" fibers and "spunbond" nonwoven webs comprise continuous fiber webs formed by extruding a molten thermoplastic material from a plurality of fine capillaries as molten threads into converging high velocity hot air streams which attenuate the filaments of molten thermoplastic material to reduce their diameter. The eductive drawing of the spunbond process also acts to impart a degree of crystallinity to the formed polymeric fibers which provides a web with relatively increased strength. By way of non-limiting example, spunbond fiber nonwoven webs and processes for making the same are disclosed in U.S. Pat. No. 4,340,563 to Appel et al, U.S. Pat. No. 5,382,400 to Pike et al.; U.S. Pat. No. 8,246,898 to Conrad et al., U.S. Pat. No. 8,333,918 to Lennon et al. and so forth.

As used herein "meltblown" fibers and "meltblown" nonwoven webs generally refer to those formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter. Thereafter, the meltblown fibers are carried by the high velocity gas stream and are deposited on a collecting surface to form a web of randomly dispersed meltblown fibers. By way of non-limiting example, meltblown fiber nonwoven webs and processes for making the same are disclosed in U.S. Pat. No. 3,849,241 to Butin, et al.; U.S. Pat. No. 4,775,582 to Abba et al., U.S. Pat. No. 4,707,398 to Wisneski et al.; U.S. Pat. No. 5,652,048 to Haynes et al, U.S. Pat. No. 6,972,104 to Haynes et al. and so forth.

As used herein, the term "machine direction" or "MD" refers to the direction of travel of the film in the method of manufacture.

As used herein, the term "cross-machine direction" or "CD" refers to the direction which is essentially perpendicular to the machine direction defined above.

As used herein, the term "elastomeric" and "elastic" refer to a material that, upon application of a stretching force, is stretchable in at least one direction (such as the MD direction), and which upon release of the stretching force, contracts/returns to approximately its original dimension. For example, a stretched material may have a stretched length that is at least 50 percent greater than its relaxed unstretched length, and which will recover at least 50 percent of its stretched dimension (i.e. the stretched length minus the original, relaxed length length) upon release of the stretching force. A hypothetical example would be a one (1) inch sample of a material that is stretchable to at least 1.50 inches and which, upon release of the stretching force, will recover to a length not less than 1.25 inches. Desirably, the material contracts or recovers greater than 60%, 65%, 70%, 75% and even more desirably, greater than 80 percent of the stretched length.

As used herein "personal care articles" means any and all articles or products used for personal health or hygiene including diapers, adult incontinence garments, absorbent pants and garments, tampons, feminine pads and liners, bodily wipes (e.g. baby wipes, perineal wipes, hand wipes, etc.), bibs, changing pads, bandages, and components thereof.

As used herein "protection articles" means all articles intended to protect a user or equipment from contact with or exposure to external matter including, for example, face masks, protective gowns and aprons, gloves, caps, shoe covers, equipment covers, sterile wrap (e.g. for medical instruments), car covers, and so forth.

Methods of making the laminates of the present invention will initially be discussed. In this regard, numerous different known film forming techniques may be used to form an elastic film suitable for use in the present invention including, for example, blowing, casting, flat die extruding, and so forth. Generally speaking, and is well known in the art, molten elastomer is extruded, thinned and chilled to form a film. After chilling the film may also be immediately drawn by stretching and thereby further reduce the thickness of the film and/or improve other properties of the film. As is known, a film may be stretched uniaxially such as in the MD or CD or, still further, may be oriented in both the MD and CD to form a biaxially stretched film. For example, the film may be clamped at its lateral edges by chain clips and conveyed into a tenter frame. In the tenter frame, the film may be drawn in the cross-machine direction to the desired draw ratio by chain clips diverging in their forward travel. As a further example, films may be stretched in the machine direction utilizing commercially available equipment such as machine direction orienters. The film may be made in-line with the other operations discussed herein or, alternatively, may be made separately and supplied via a supply roll.

In reference to the process and system shown in FIG. 1, an elastomeric film 10 is provided and unwound from a first supply roll 12. The elastomeric film 10 travels away from the first supply roll 12 and towards a first roller assembly 22 that includes first roll 22A and second roll 22B. The pair of rolls 22A and 22B are positioned proximate one another so as to form a nip 21 and rotate in opposite directions as indicated by the corresponding arrows. The circumferential speed (S2) of the first roller assembly 22 and corresponding drive rolls 22A, 22B is approximately the same as the speed (S1) of the unwind roll 12; although as is known in the art the speeds may vary slightly as desired to maintain a small degree of tension or slack on the film to facilitate handling. The elastomeric polymer film 10 passes through the nip 21 of the first roller assembly 22 and travels in the direction towards and enters a nip 27 of a second roller assembly 26 comprising a pair of drive rollers 26A, 26B.

The circumferential speed (S3) of the second roller assembly 26 and corresponding drive rolls 26A, 26B is higher than the circumferential speed (S2) of the first roller assembly 22 and its drive rollers 22A, 22B. Thus, as it travels between the first and second roller assemblies 22, 26 the elastomeric film 25 is elongated or stretched in the MD. In certain embodiments, the peripheral speed of the downstream roller assembly (S3) can be at least 150%, 250%, 300% or 400% higher than the peripheral speed of the upstream roller assembly (S2). In still further embodiments, the peripheral speed of the downstream roller assembly, e.g. assembly 26, can be between about 200 and about 1200%, about 250% and about 1000% or even between about 300% and about 900% of the peripheral speed of the upstream roller assembly.

It will be appreciated that the degree of stretching of the elastic film may be achieved in a single stretching operation or in a plurality of discrete stretching operations. For example, in an alternate embodiment, the speed (S1) of the supply roll 12 could optionally be slower than the speed (S2) of the first roller assembly 22 thereby having a first stretching operation stretching elastic film 10 between roller assemblies 12 and 22 and a second stretching operation stretching elastic film 25 between roller assemblies 22 and 26. The number and degree of individual stretching operations can vary to achieve the desired degree of overall stretch. In this regard, prior to entering the nip of the grooved roll assembly the elastomeric film may be elongated or stretched an overall amount of at least about 2.5×, 3×, 4× or even 5× in the MD and in certain embodiments stretched not more than about 12×, 10×, or even 9× in the MD. The roll assemblies and/or equipment utilized to stretch the film is not believed limited and may be stretched using conventional film-orientation units or machine direction orienters, such as those commercially available from Parkinson Technologies, Inc.

In addition to the elastomeric film, at least one support material, such as a fabric, is employed as a facing material for laminating to the elastomeric film. In this regard, the fabric may comprise one or more fibrous materials having desired physical attributes, such as pleasing hand, softness, improved aesthetics, tensile strength and so forth. The fabrics may be made in-line with the elastomeric polymer film and/or provided from a supply roll. In reference to FIG. 1, a first fabric 14 may be unwound from a second supply roll 16 and directed towards the nip 27 of the second roller assembly 26. The first fabric 14 is superimposed with the stretched elastomeric polymer film 25 prior to or immediately upon entering the nip 27. Often it will be desirable for the laminate to have an outer facing on both sides of the elastic and resulting composite elastic laminate. Thus, a second fabric 18 may simultaneously be unwound from a third supply roll 20 and likewise directed towards the nip 27 of the second roller assembly 26. However, while the second fabric 18 is also superimposed with the stretched elastomeric film prior to or immediately upon entering the nip 27, it is positioned against the underlying or opposite side of the elastomeric film 25 such that the elastomeric film 25 is positioned between the opposed outer fabrics 14, 18. The multiple superposed layers 14, 25, 18 together form a sheet stack. Unlike the elastomeric film 10, the nonwoven webs 14, 18 are not significantly stretched as they travel between their respective supply rolls 16, 20 and the grooved roll assembly 30. In this regard, the circumferential sped (S3) of the supply rolls 16, 18 is substantially similar to that of the second roller assembly 26 and grooved roll assembly 30.

The sheet stack is directed into the nip 31 of the grooved roll assembly 30 having first and second inter-meshing grooved rolls 30A, 30B. The circumferential speed (S3) of the grooved roll assembly 30 can be substantially the same as that of the second roller assembly 26 so as to maintain the elastic film in a stretched condition when entering the grooved roll assembly 30. In an alternate embodiment, the grooved roll assembly 30 can operate at a circumferential speed higher than that of the second roller assembly 26 assembly thereby further machine direction stretching the elastic film and also neck stretching of the nonwoven webs prior to entering the grooved roll assembly 30.

Figure 3:
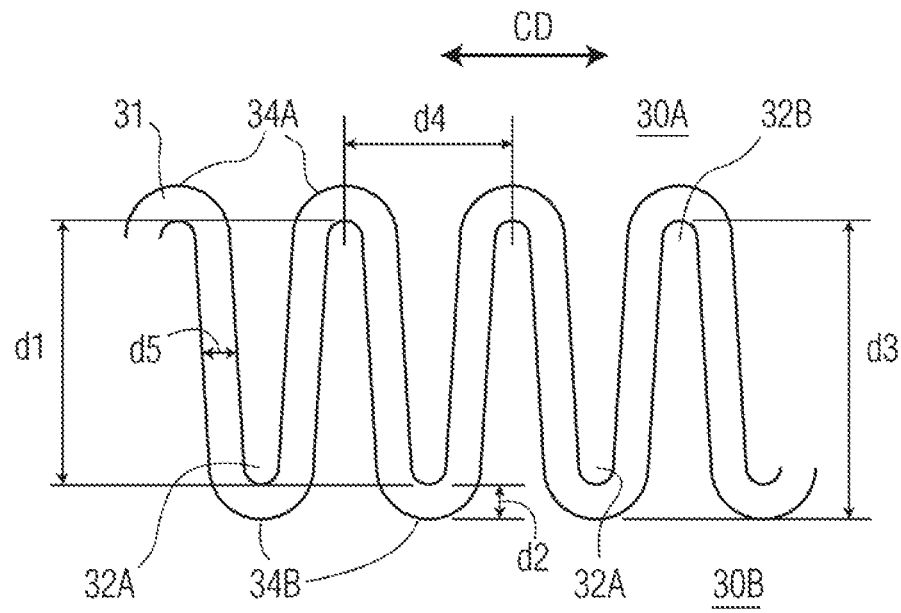
FIG. 3 is a magnified view of a section of a grooved roller assembly suitable for use in forming elastic laminates of the present invention.
Figure 3A:
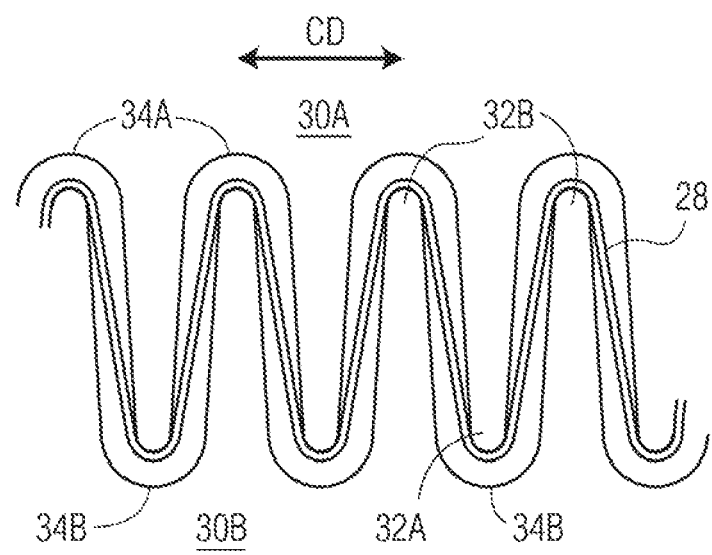
FIG. 3A is a magnified view of the grooved roll section of FIG. 3 containing a nonwoven/film/nonwoven stack.

In addition to the MD stretch and tension imparted by the upstream assemblies, a CD stretch is imparted on the stacked film and nonwoven webs within the grooved roll assembly 30. This multi-dimensional strain is believed to cause a controlled rupturing of the film. As best seen in reference to FIGS. 3 and 3A, the inter-meshing grooved rolls 30A, 30B form an irregular nip 31 and each roller includes a series of alternating ridges 32 and grooves 34. The rolls 30A, 30B are arranged such that their respective ridges 32A, 32B and grooves 34A, 34B are off-set from one another and inter-mesh.

In other words, the ridges 32A of the upper grooved roll 30A are positioned so as to extend into the grooves 34B of the second or lower grooved roll 30B and between the ridges 32B of the second grooved roll 30B. Similarly, the ridges 32B of the second grooved roll 30B are positioned so as to extend into the grooves 34A of the first grooved roll 30A and between the ridges 32A of the first grooved roll 30A. In certain embodiments, the ridges and grooves run concentrically around the entirety of the rolls 30A, 30B. The grooves or troughs of such grooved rolls may be machined into a roll, may be formed by a series of elements such as discs, or may be any other means that provides the functional structure shown.

As the stack 28 is pulled through the nip 31 the engagement at the ridges 32A, 32B of the opposed rolls 30A, 30B causes the components forming the stack 28 to be stretched in the widthwise or cross-machine direction. The biaxial stretching forces and heat also act together act to cause the regionally controlled rupturing of the elastic film. In addition, in the areas on or about the top of the ridges, pressure and heat is applied via the rolls which also facilitates bonding between one of more layers within the stack. With respect to the use of such inter-meshing grooved roll assemblies, the amount of CD stretch imparted to the unengaged sections, and the amount of pressure imparted to the engaged sections atop the ridges, is a function of the engagement depth to which the grooved rolls are set; the deeper the grooved rolls mesh, the greater is the percent extension in the CD. The opposed grooves and ridges engage or mesh with one another to a selected depth (d1). Further, by arranging the gap distance (d2) between the rolls, the nonwoven material can be acted upon to varying degrees.

The engagement depth (d1) can be at least about 5 mm and in certain embodiments may be between about 5 mm and about 20 mm or between about 6 mm and about 15 mm. The CD stretch imparted to the material in the grooved roll assembly desirably causes the CD width of the outer nonwoven fabrics to increase at least about 5% and in certain embodiments can result in the CD width of the outer nonwoven fabrics increasing between about 5-20%, between about 5-15%, between about 8-15% or even between about 6-12%.

The depth of the groves and/or the height of the ridges (d3) can vary considerably as it is the engagement depth (d1) that more directly drives the degree of CD stretch. However, the depth and height of the ridges and grooves is selected relative to the stack height so as to ensure that the stack is not significantly pinched or severed while within the grooved roll nip. In order to effectively engage the sheet stack 28 while in the nip 31 without severing the stack, neither the nip gap distance between the opposed grooves and ridges, the apex nip gap (d2), nor the nip gap distance between sidewalls of adjacent ridges, the side nip gap (d5), is substantially smaller than the height of the stack 28. The height of the stack or 'stack height' being measured by placing each of the sheets of appropriate size upon one another and measuring in accordance with the method for measuring fabric thickness as described herein. The apex nip gap (d2) may be slightly smaller than the stack height but is desirably not less than 100% of the stack height. In certain embodiments, the apex nip gap (d2) and side nip gap (d5) are each at least 100% the stack height and in further embodiments is at least 110%, 120%, 150% or even 200% of the stack height. In certain embodiments, the side nip gap (d5) may be larger than the apex nip gap (d2). In addition, the shape of the top of the ridges 32A, 32B are desirably rounded including for example having a substantially semi-circular shape.

It will be apparent that the number of engaging ridges and the frequency of the ridges may be greatly varied. By way of example only, ridges having a height (d3) between about 0.5 cm and about 2 cm will be suitable for many embodiments having relatively lower basis weight materials. In certain embodiments, a single roll may have between about 0.25 ridges per cm and about 7 ridges per cm, and in some embodiments from about 0.5 ridges per cm and 5 ridges per cm, and in still other embodiments between about 1 and about 4 ridges per cm. In addition, the peak-to-peak distance (d4) of the ridges can also vary such as in certain embodiments being between about 4 cm to about 0.2 cm, and in other embodiments being between about 3 cm to about 0.25 cm, and in still further embodiments being between about 2 cm and about 0.5 cm. Still further, in certain embodiments the frequency or spacing of the ridges may vary across the CD length of the roll.

In order to achieve bonding as between the layers and rupturing of the film, adequate stretching forces and heat is applied to the outer fabric layers and elastic film. Upon rupturing, the film will retract to some degree allowing the opposed nonwoven webs to directly contact one another. However, the temperature of the facings and film layers should not be so high such that it causes, together with the pressures applied via the stretching forces, the film and/or fibers to melt a significant amount. In this regard, if the film melts and fibers become fully embedded in the film elasticity of the resulting laminate will be degraded. Further, if fibers are significantly melted and compressed into film-like segments this can create hard spots and/or areas that provide a generally rougher hand-feel.

Heating of the layers may be achieved by any one of various means known in the art. In certain embodiments, the stack may be heated immediately prior to entering the nip of the grooved roll assembly such as by the use of heated rolls, IR heaters, convection heaters, etc. With respect to the embodiment depicted in FIG. 1, one or more rolls of the first and/or second roll assemblies 22, 26 can be heated. Additionally and/or alternatively, the layers may be heated while against the grooved rolls by heating one or both of the grooved rolls 30A, 30B. When using the grooved rolls to heat the layers, it will be appreciated that one or more of the layers may be directed along a section of the outer perimeter of a roll prior to entering the nip in order to increase the length of time the layer directly contacts and is heated by the roller.

In one aspect, with respect to the use of olefin elastomers, one or both of the grooved rolls can be heated to a temperature between about 65° C.–145° C., between about 70° C.–120° C. or between about 80-98° C. However, it will be appreciated that the temperature of the one or more rollers will vary with respect to various factors including the speed of the stack, the softening points of the polymers used and the force applied to the materials. In certain embodiments, at least one or both grooved rolls are heated to a temperature of at least about 5° C., 10° C., 15° C. or even 20° C. higher than the Vicat softening temperature of the elastomeric film. In certain embodiments, one or both rolls may be between about 5-90° C., 10-75° C. or even 10-50° C. higher than the Vicat softening temperature of the elastomeric film. Further, in certain embodiments both rolls can be heated but to a temperature below the melting temperature of the nonwoven fabrics. The Vicat softening temperature may be determined in accordance with ASTM D1525-09.

After having been bonded together in the grooved roll assembly 30, a cohesive laminate 40 is formed. The laminate can thereafter be directly fed into a converting line for incorporation into the desired end product. Alternatively, as shown in FIG. 1, the laminate can be wound on a winder roll 42 for future use and/or converting. The elastic laminate 40 will often be wound onto the supply roll 42 in a tensioned state. However, in order to limit the loss of elasticity it will often be desirable to allow the laminate to substantially retract prior to being wound on the winder roll. In this regard, the winder roll 42 can have a peripheral speed (S4) that is less than the peripheral speed (S3) of the grooved roll assembly 30. In certain embodiments, the peripheral speed of the roller assembly downstream from the grooved rolls can be 80% of the peripheral speed of the grooved rolls. For example, the peripheral speed (S4) of the winder roll 42 may be between about 15% and about 75%, or even between about 35% and about 65%, of the peripheral speed (S3) of the grooved roll assembly 30.

Figure 2:
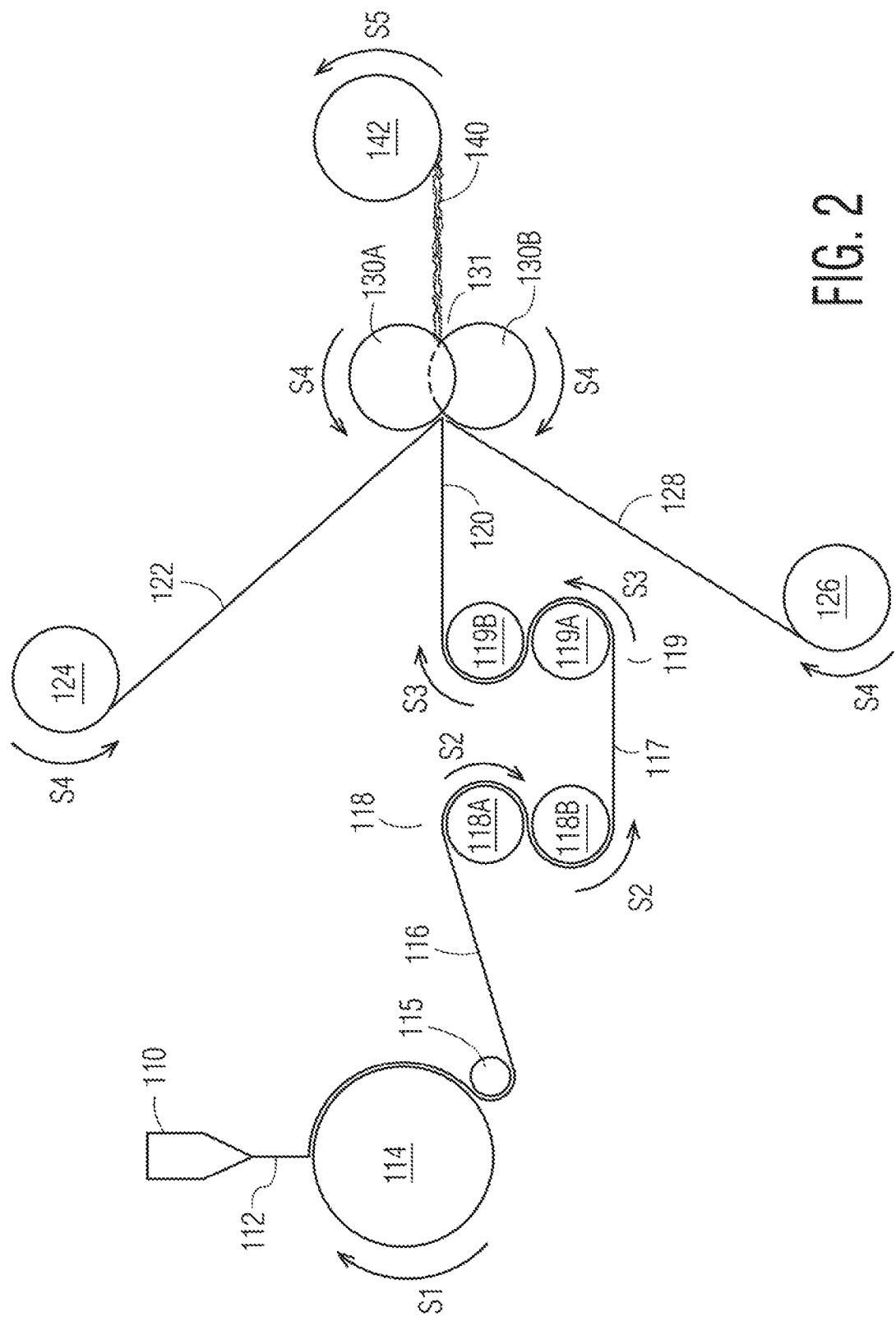
FIG. 2 is a schematic illustration of an alternate method for forming an elastic laminate of the present invention.

In an alternate embodiment, and in reference to FIG. 2, elastomeric polymer is fed from a hopper (not shown), melted and directed to an extrusion apparatus 110 such as a film die. The extruded polymer 112 is directed onto a chill roll 114 to form a single-layered elastic film 116. If a multilayer film is to be produced, the multiple layers may be co-extruded together and directed onto the chill roll. Typically, the chill roll 114 is kept at a temperature sufficient to solidify and quench the extruded polymer and form a film thereon. In certain embodiments, the chill roll may be maintained at a temperature between about 20° C. to 60° C.

To achieve the desired elastic properties of the film, various parameters of the film formation and stretching operation are selectively controlled as are known in the art. For example, as is commonly known, the circumferential speed of the chill roll may be higher than the extrusion speed of the molten polymer exiting the film die. This disparity in rates causes the film to stretch and/or orient to a certain degree in the MD. After formation of the film on the chill roll, the film may be drawn or stretched in the MD as generally described above. In some embodiments, for example, the formed film is cumulatively stretched in the machine direction at a draw ratio of from about 3 to about 12, in some embodiments from about 3 to about 9, and in some other embodiments from about 4 to about 7. The draw ratio may be determined by dividing the linear speed of the film exiting the stretching operation by the linear speed of the film entering the stretching operation.

In reference to the embodiment depicted in FIG. 2, the elastic film 116 is stretched in the machine direction by passing through a series of rolls with the downstream rolls traveling at a relatively higher circumferential speed than the preceding upstream rolls. In this regard, the elastic film 116 is directed from the chill roll 114 and cooperating guide roll 115 to an s-wrap roller assembly 118 comprising at least stacked first and second rollers 118A, 118B. The rolls 118A, 118B of the s-wrap assembly operate at circumferential speed (S2) that is faster than the circumferential speed (S1) of the chill roll 114. This speed differential acts to stretch the elastic film 116 in the machine direction. Optionally, the stretched elastic film 116 film may then be directed to a further downstream drive roll assembly 119, including stacked first and second rollers 119A, 119B, operating a circumferential speed (S3) that is greater than the circumferential speed (S2) of the upstream or first roller assembly 118. This operation imparts further incremental stretching and elongation of the elastic film 117. While two sets of roller assemblies are illustrated as part of the system depicted in FIG. 2, it should be understood that the number of assemblies may vary as desired, depending on the overall level of stretch that is desired and the degrees of stretching between each of the assemblies.

The stretched film 120 exits the s-wrap rollers 119A, 119B and is then directed to a further downstream roller assembly, in this case a groove roll assembly 130 having inter-meshing grooved rolls 130A, 130B. The outer facing materials 122, 128 are directed to be superimposed with the elastic film 120, forming a fabric/film/fabric stack just prior to entering the nip 131 of the grooved roll assembly 130. In this regard, the outer fabrics may optionally be made in-line with the elastic film and/or provided from a supply roll. In reference to FIG. 2, a first nonwoven fabric 122 is unwound from a first supply roll 124 and a second nonwoven web 128 may be unwound from a second supply roll 126. The nonwoven webs 122, 128 may then be directed to be in superposition with opposite surfaces of the elastic film 120 just prior to entering the nip 131 of grooved roll assembly 130.

The circumferential speed (S3) of the upstream roller assembly 119 is lower than the circumferential speed (S4) of the grooved rollers 130A, 130B. Thus, as a result of the speed differential, the film 120 is further elongated in the machine direction and in a stretched state as it enters the nip 131 of the grooved roll assembly 130 together with the nonwoven fabrics 122, 128. As discussed above, as a result of the heat and engagement with the grooved rolls, the stack is both stretched in the CD and cohesively bonded together.

In the present embodiment as shown in reference to FIG. 2, the composite elastic laminate 140 is thereafter wound on the winding roll 142 while under substantially reduced MD tension. In this regard, composite laminate 140 is kept under sufficient tension for processing but is allowed to substantially retract by employing a slower circumferential speed (S5) for the take-up roll 142 relative to the speed (S4) of the upstream grooved rolls 130A, 130B. In this regard, the elastic composite may be allowed to retract between about 10% and about 80% or between about 15% and about 65%. Because the elastic film 120 is tensioned prior to lamination, upon exiting the grooved rolls and relaxing it will retract toward its original pre-stretched machine direction length and become shorter in the machine direction, thereby causing the bonded nonwoven webs to form gathers in the composite. The resulting elastic laminate thus becomes extensible in the machine direction at least to the extent that the gathers or buckles in the web may be pulled back out flat and allow the elastic film to elongate.

As noted above, the engagement of the sheet stack within the grooved rolls causes the materials to be stretched in the CD. The combined CD and MD stretching forces also act to rupture and permanently displace the film. Further, it is believed that once torn or ruptured, the elastic film retracts about the tear or rupture to form individual and/or discrete apertures within the film. Thus, the elastic laminate will include a series of alternating first and second segments extending in the machine direction or substantially in the machine direction; the first segments comprising a continuous or substantially continuous film strip extending in the MD and second segments between the first that are strewn with apertures of random shape, size and/or location.

Figure 4:
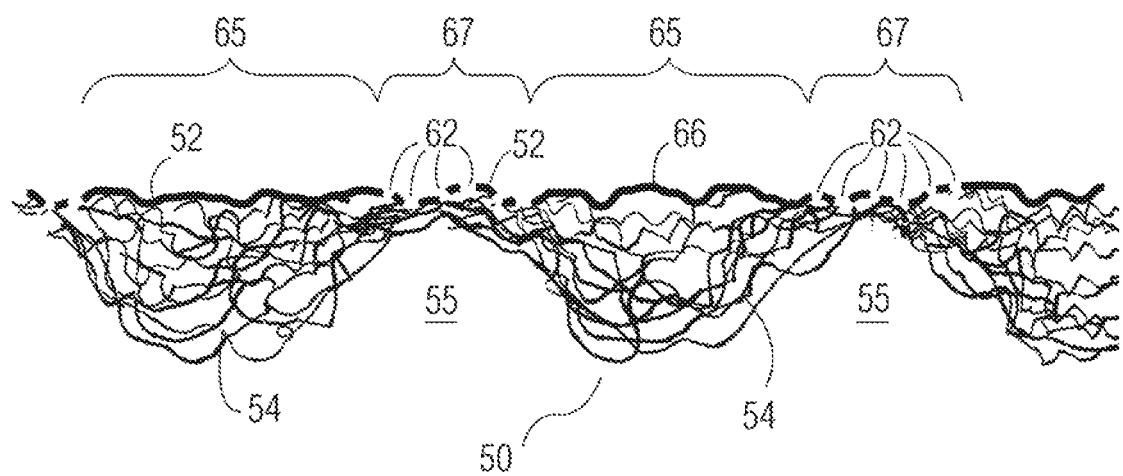
FIG. 4 is a CD cross-sectional view of a section of a two-layer elastomeric laminate of the present invention.
Figure 5:
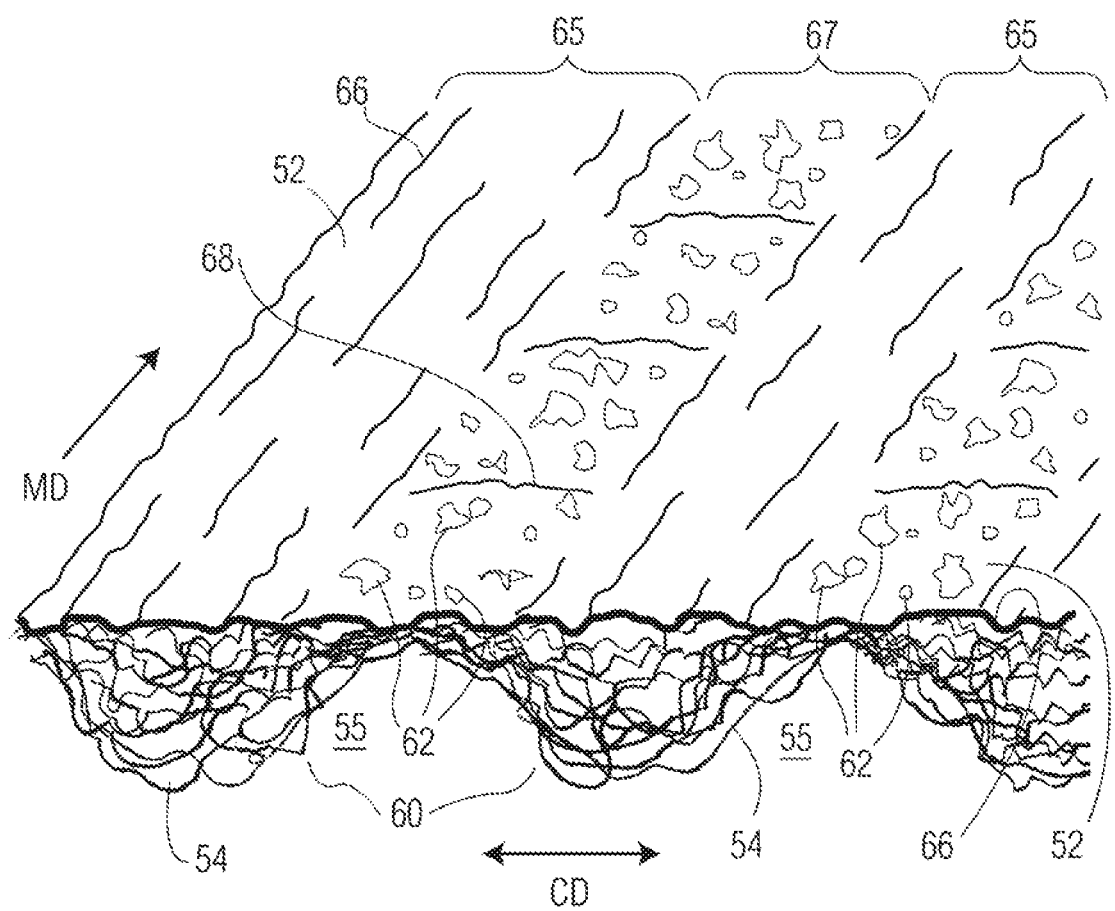
FIG. 5 is a perspective view of a section of a two-layer elastomeric laminate of the present invention with the film layer facing up.

In reference to FIGS. 4 and 5, the elastic laminate 50 a continuous elastomeric film 52 bonded to a fabric 54 such as, for example, a spunbond fiber nonwoven web. The fabric 54 and elastomeric film 52 both span the CD. However, the nature or character of the elastomeric film differs across the CD and forms a series of distinct bands or segments extending in the MD. In this regard, the elastic laminate 50 has first and second segments 65, 67 that alternate across the cross-direction and that extend continuously along the machine direction. The first segments 65 include a continuous band or strip of film 52 that lacks or is substantially devoid of apertures. The second segments 67 include a strip or band of elastomeric film 52 that is strewn with discrete, apertures 62. The aggressive biaxial stretching causes the formation of apertures 62 as noted above. The apertures 62 are entirely or predominantly located in second bands or segments 67 that extend in the machine direction. Within these machine direction extending segments 67, the apertures 62 are of irregular size and shape and also random location within this second band 67.

The manner in which the film is strained within the grooved rollers and also the manner in which it retracts upon exiting the grooved rollers, differs regionally as noted above and may result in a film with additional unique regional structures. As best seen in reference to FIG. 5, the CD retraction of the elastic film 52 in the first regions 65 can result in the formation of a plurality of micro-gathers or micro-furrows 66 extending in or substantially in the machine direction, i.e. where the longer dimension of the furrow or fold would extends parallel with the machine direction. For purposes herein, 'substantially aligned with' or 'substantially extending in' the machine direction include those directions that are parallel with the machine direction as well as those that are +/−30 degrees of the machine direction. Similarly, 'substantially aligned with' or 'substantially extending in' the cross direction includes those directions that are parallel with the cross direction as wells as those that are +/−30 degrees of the cross direction. In addition, the film displacement and aperturing that occurs as a result of the high stretching forces experienced in the second regions 67, can result in the formation of puckers 68 within the second segments 67. These puckers are aligned with or are substantially aligned with the cross-direction. In certain embodiments, the areas between the puckers can have a higher density of apertures and/or can comprise a large continuous aperture.

The laminate 50 and/or fabric 54 layer may also vary across the CD. For example, the laminate may be experience greater compression regionally and have a thickness in the first segments 65 that are significantly larger than that in the second regions 67. The average basis weight in the first regions can also be significantly greater than that of the second regions. In certain embodiments, the average basis weight of the first regions can be about 10%, 15%, 20% or even 25% greater than that of the second regions. In this regard, the disparate pressures, temperatures and stretching forces also can cause the laminate to form furrows or grooves 55 that are aligned with or substantially aligned with the machine direction. In its untensioned and retracted state, the laminate 50 may also have a plurality of puffed regions 60 that define relatively lower-density segments of the fabric layer 54, i.e. areas in which the fabric is more open and/or the fibers have greater inter-fiber spacing. The alternating series of grooves and puffed segments presents a generally corduroy appearance.

The extensible fabric layers can also have a series of gathers extending in or substantially in the CD. As noted above, when extended, these gathers flatten and allow the laminate to extend in the MD; once the stretching force is removed the elastic film causes the laminate to retract and resume its original gathered shape.

Figure 6A:
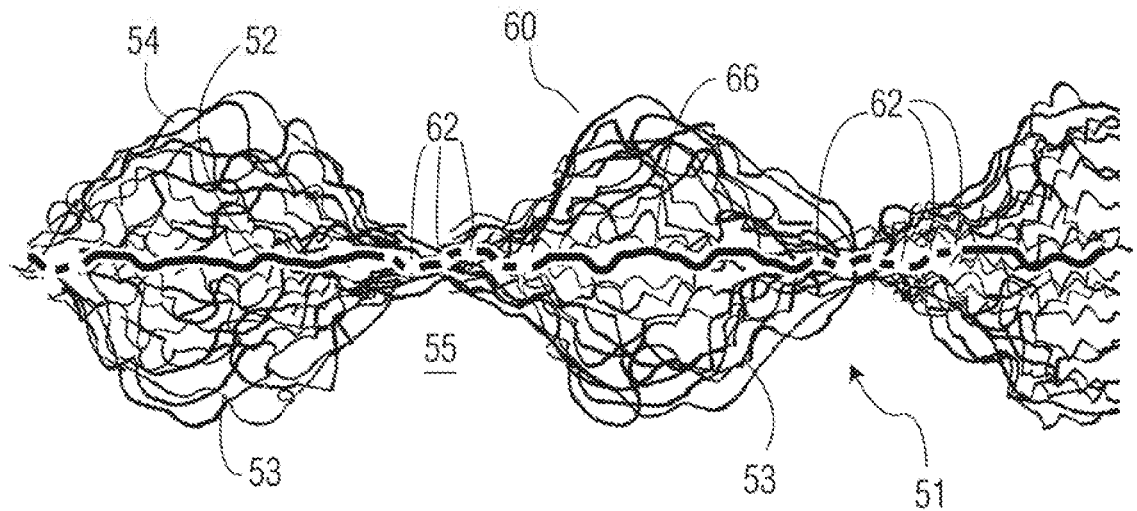
FIG. 6A is a cross-machine direction cross-sectional view of a section of a three-layer elastomeric laminate of the present invention.
Figure 6B:
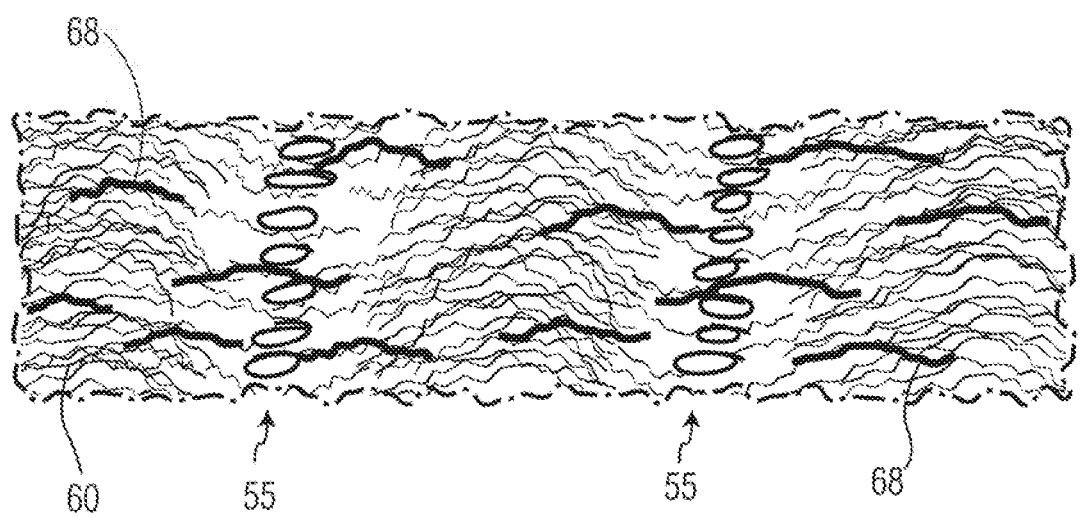
FIG. 6B is a perspective view of a section of a three-layer elastomeric laminate of FIG. 6A.

As discussed above it will often be desirable to have a facing layer attached to both of the major surfaces of the elastic film. In this regard, as seen in reference to FIGS. 6A and 6B, a three layer laminate 51 is provided having an elastic film 52 with a first fabric 54 attached to one side of the elastic film 52 and also a second fabric 53 attached to the opposite side of the elastic film 52. The opposed facing layers can be bonded to the film and/or to one another in the segments 67 where the elastic film 52 is strewn with apertures 62. Within the outer fabric layer 54 and 53, numerous gathers 67 exist extending substantially in the CD.

The first and second segments can each be present in the laminate in a frequency along the cross-direction greater than 0.5 per cm and desirably a frequency greater than about 1, 1.5, 2, 2.5 or 3 per cm. Further, the frequency in the cross-direction of the first and second sections can be less than about 14, 12, 10, 8 or 6 per cm. In certain embodiments, the first and second segments may have a dimension or width in the cross-direction of at least about 0.07 mm, 0.08 mm, 0.1 mm, 0.13 mm, or 0.17 mm. Further, the first and second segments may have a cross-direction dimension of less than about 20 mm, 10 mm, 5 mm, 3 mm, or 2 mm. As generally described above, the forces applied to the layers at and about the apex of the ridges differ from those impacting the layers that do not directly contact and engage the ridges (i.e. those areas spanning or extending between the ridges). In addition, depending on the selected grooved roll design, the relative size of the sections that contact the ridges may differ from the size of those not contacting the ridges. Therefore, the width of the first and second segments as measured in the cross-direction may differ from one another; for example the first segments may have an average width that is larger or smaller than that of the second segments. In certain embodiments, the first segments can have an average width, as measured in the cross-direction that is at least 10%, 15%, 20% or 25% larger than that of the second segments. Further, the first segments can have an average width, as measured in the cross-direction, that is not more about 100%, 80%, 60%, or 45% larger than that of the second segments. In certain embodiments, the elastic film extends continuously across at least about 75%, 80%, 85%, 90%, 95% or even about 98% of the length of the laminate in the cross-machine direction. Additionally and/or alternatively, the first regions and/or the second regions extend continuously along the length of the laminate in the machine direction along at least about 80%, 85%, 90%, 95% or even about 98% of the length of the laminate in the machine direction.

In certain embodiments, the elastic laminate can have, as fully contracted and in an unstretched state, a basis weight of at least about 15 $g/m^2$ and in certain embodiments may have a basis weight of at least about 25, 30, 35 or 40 $g/m^2$ and less than about 120, 90, 75, 65 or 60 $g/m^2$. In certain embodiments, in a relaxed and unstretched state, the elastic film can comprise at least 10% by weight of the laminate such as for example comprising at least 10%, 15%, 20%, 25%, 30%, 35%, 40% or 45% of the laminate. Further, in a relaxed and unstretched state, the elastic film can comprise less at least about 10% by weight of the laminate such as for example comprising at least about 10%, 15%, 20%, and 25% of the laminate. Further, in a relaxed and unstretched state, the elastic film can comprise less than about 45%, 40%, 35% or even 30% by weight of the laminate. The outer fabric(s) may comprise between about 55-90%, by weight of the laminate such as comprising at least about 55%, 60%, 65% or 70% by weight of the laminate and/or comprising less than about 90%, 85%, 80% or 75% by weight of the elastic laminate. In addition, in view of the many permanently formed apertures in the first segments, the film and laminate can have excellent air permeability and breathability and in certain embodiments may have an air permeability between about 150-1000 CFM, between about 200-700 CFM or between about 225-500 CFM.

In addition, despite the relatively low basis weights and excellent breathability, the elastic laminates provide desirably elastic properties. In this regard, the elastic laminates can provide for and have a percent stretch at 2000 g-f of greater than about 75%, 80%, 85%, 90%, 95% or even 100%. Additionally and/or alternatively, the elastic laminate can provide or have a percent stretch at 2000 g-f of less than about 260%, 255%, 250%, 245%, 340% or even 235%.

A wide variety of elastic films are believed suitable for use in connection with the present invention. In this regard, elastic films can comprise either monolayer or multi-layer films. Further, a variety of different elastomeric polymers, and blends thereof, are believed suitable for use in the present invention. In certain embodiments, the elastomeric films and corresponding polymers predominantly comprise thermoplastic polymers having a softening point below that of the fabrics forming the outer layers. Generally, the polymeric portion of the elastic film will desirably comprise greater than 85%, 90%, 92%, 95%, or 98% elastomeric polymer(s). The specific type and amounts of elastomer selected will vary with the desired properties including, in particular, the elastic properties such as the % stretch and recovery force. Any of a variety of thermoplastic elastomers may generally be utilized as the elastic film of the elastic composite laminate of the present invention. Such polymers include elastomeric polyesters, elastomeric polyurethanes, elastomeric polyamides, elastomeric styrenic polymers, elastomeric polyolefins, and so forth.

In certain embodiments, the polymeric portion of the film elastic film can comprise, predominantly or entirely, olefin elastomers such as comprising greater than 55%, 75%, 85%, 90%, 95% or 97% elastomeric olefin polymers. In one aspect, the elastic film can comprise semi-crystalline polyolefin polymer(s). Semi-crystalline polyolefins have or are capable of exhibiting a substantially regular structure. For example, semi-crystalline polyolefins may be substantially amorphous in their undeformed state, but form crystalline domains and/or increased polymer chain alignment upon stretching. The degree of crystallinity of the olefin polymer may be from about 3 percent to about 30 percent, in some embodiments from about 5 percent to about 25 percent, and in some embodiments, from about 5 percent and about 15 percent. The semi-crystalline polyolefin may have a melting temperature of from about 40° C. to about 120° C., in some embodiments from about 45° C. to about 90° C., and in some embodiments, from about 50° C. to about 80° C.

Particularly suitable polyethylene copolymers are those that are "linear" or "substantially linear." The term "substantially linear" means that, in addition to the short chain branches attributable to comonomer incorporation, the ethylene polymer also contains long chain branches in the polymer backbone. "Long chain branching" refers to a chain length of at least 6 carbons. Each long chain branch may have the same comonomer distribution as the polymer backbone and be as long as the polymer backbone to which it is attached. Preferred substantially linear polymers are substituted with from 0.01 long chain branch per 1000 carbons to 1 long chain branch per 1000 carbons, and in some embodiments, from 0.05 long chain branch per 1000 carbons to 1 long chain branch per 1000 carbons. In contrast to the term "substantially linear", the term "linear" means that the polymer lacks measurable or demonstrable long chain branches. That is, the polymer is substituted with an average of less than 0.01 long chain branch per 1000 carbons.

Exemplary semi-crystalline polyolefins include polyethylene, polypropylene, blends and copolymers thereof. In one particular embodiment, an ethylene polymer is employed that is a copolymer of ethylene and an alpha-olefin, such as a $C_3$-$C_{20}$ alpha-olefin or $C_3$-$C_{12}$ alpha-olefin. Suitable alpha-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired a-olefin comonomers are 1-butene, 1-hexene and 1-octene. The ethylene or propylene content of such copolymers may be from about 60 mole percent to about 99 mole percent, in some embodiments from about 80 mole percent to about 98.5 mole percent, and in some embodiments, from about 87 mole percent to about 97.5 mole percent. The alpha-olefin content may likewise range from about 1 mole percent to about 40 mole percent, in some embodiments from about 1.5 mole percent to about 15 mole percent, and in some embodiments, from about 2.5 mole percent to about 13 mole percent. Ethylene polymer elastomers can have a density of from about 0.85 g/cm$^3$ to about 0.90 g/cm$^3$, and in certain embodiments between about 0.86 to about 0.89 g/cm$^3$.

Any of a variety of known techniques may generally be employed to form the elastomeric polyolefins. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Olefin elastomers and methods of making the same are described, for instance, in U.S. Pat. No. 5,272,236 to Lai et al., U.S. Pat. No. 5,278,272 to Lai et al., U.S. Pat. No. 5,472,775 to Obijeski et al., U.S. Pat. No. 5,539,056 to Yang et al., U.S. Pat. No. 7,582,716 to Liang et al., the contents of which are incorporated herein in by reference to the extent consistent herewith.

Exemplary commercially available polyolefin-based thermoplastic elastomers suitable for use in the elastomeric film include VISTAMAXX™ (propylene-based elastomer, available from ExxonMobil Chemical, Houston, Tex.), INFUSE™ (olefin block copolymers, available from Dow Chemical Company, Midland, Mich.), VERSIFY™ (propylene-ethylene copolymers, available from the Dow Chemical Company, Midland, Mich.), ENGAGE™ (ethylene octane copolymer, available from Dow Chemical, Houston, Tex.), and NOTIO 0040 and NOTIO 3560 (available from Mitsui Chemical (USA), New York, N.Y. In one particularly suitable embodiment, the polyolefin-based thermoplastic elastomer is VISTAMAXX™ 6102FL.

In addition, also believed suitable are elastomers comprising block copolymers such as those that contain blocks of a monoalkenyl arene and a saturated conjugated diene. The monoalkenyl arene block(s) may include styrene and its analogues and homologues, such as o-methyl styrene; p-methyl styrene; p-tert-butyl styrene; 1, 3 dimethyl styrene p-methyl styrene; etc., as well as other monoalkenyl polycyclic aromatic compounds, such as vinyl naphthalene; vinyl anthrycene; and so forth. Preferred monoalkenyl arenes are styrene and p-methyl styrene. The conjugated diene block(s) may include homopolymers of conjugated diene monomers, copolymers of two or more conjugated dienes, and copolymers of one or more of the dienes with another monomer in which the blocks are predominantly conjugated diene units. Preferably, the conjugated dienes contain from 4 to 8 carbon atoms, such as 1,3 butadiene (butadiene); 2-methyl-1,3 butadiene; isoprene; 2,3 dimethyl-1,3 butadiene; 1,3 pentadiene (piperylene); 1,3 hexadiene; and so forth. The amount of monoalkenyl arene (e.g., polystyrene) blocks may vary, but typically constitute from about 8 weight percent to about 55 weight percent, in some embodiments from about 10 weight percent to about 35 weight percent, and in some embodiments from about 15 weight percent to about 25 weight percent of the copolymer. Thermoplastic elastomeric copolymers of this type are available from Kraton Polymers LLC of Houston, Tex. under the trade name Kraton™. Kraton™ polymers include styrene-diene block copolymers, such as styrene-butadiene, styrene-isoprene, styrene-butadiene-styrene, styrene-isoprene-styrene, and styrene-isoprene/butadiene-styrene. Kraton™ polymers also include styrene-olefin block copolymers formed by selective hydrogenation of styrene-diene block copolymers. Examples of such styrene-olefin block copolymers include styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene. Also suitable are polymers composed of an A-B-A-B tetrablock copolymer such as, for example, a styrene-poly(ethylene-propylene)-styrene-poly(ethylene-propylene) ("S-EP-S-EP") block copolymer. Various suitable styrenic block copolymers are described in, but not limited to, U.S. Pat. No. 4,663,220 to Wisneski et al., U.S. Pat. No. 5,093,422 to Himes, U.S. Pat. No. 5,332,613 Taylor et al., U.S. Pat. No. 8,604,129 Thomas, and U.S. Pat. No. 8,980,994 Wright et al.

In certain embodiments the film extrudate and corresponding elastic film can comprise a mixture of one or more different elastic polymers. By way of example, blends comprising a mixture of styrenic block co-polymers together with polyolefin elastomers are well suited for use in connection with the present invention. Blends comprising between 55-95% polyolefin elastomer(s) and 5-45% styrenic block co-polymer(s) provide a good combination of retractive force and cost. Alternatively, blends comprising between 5-45% polyolefin elastomer(s) and 55-95% styrenic block co-polymer(s) provide excellent stretch and recovery properties. Still further, in certain embodiments the film extrudate and corresponding elastic film can comprise a mixture of one or more elastic polymers together with a minor portion of inelastic polymers. By way of example, the elastomeric polymer composition may include a mixture of semi-crystalline ethylene and propylene polymers. For example, in certain embodiments the elastomeric polymer, such as an ethylene polymer, comprises between about 80 and about 99% or between about 85 and about 95% of the polymeric portion of the extrudate and film and the inelastic polymer, such as a propylene polymer, comprises between about 1 and about 20% or between about 5 and about 15% of the polymeric portion of the extrudate and film.

The film may also include additional components as desired to achieve or enhance various properties. For example, in addition to the elastomeric polymers, the film may optionally also include fillers, colorants, plasticizers, tackifiers, antioxidants, and/or other know additives. In certain embodiments, the film may include opacifying fillers or colorants, such as for example $TiO_2$, in an amount between about at 0.1 to about 5% by weight or between about 0.5 or to about 3% by weight of the film extrudate and/or elastic film. In still further embodiments, heat and/or UV stabilizer packages may be used, for example Eastman Regalrez 1049 or 1126, in amounts between about 2-10 wt. % of the film extrudate and/or elastic film.

At least one support material, such as a fabric, is employed as an outer facing of the multi-layer composite. Fabrics utilized in association with the present invention will be porous in nature providing numerous direct or tortuous pathways there through. In this regard, the fabric may comprise one or more fibrous materials having desired physical attributes, such as pleasing hand, softness, tensile strength and/or other desired attributes. Importantly, the fabric provides CD strength properties to the elastic laminate necessary for the associated processing, converting, and manufacturing of the ultimate article and/or for sufficient durability in use. In this regard, the fabric desirably has a tensile strength of at least about 50 g-f including for example having a tensile strength greater about 100 g-f, 150 g-f, 200 g-f, 250 g-f or even 300 g-f and, in certain embodiments, a tensile strength less than about 5000 g-f, 3000 g-f, 2500 g-f, 2000 g-f or even 1500 g-f. In addition, the fabric desirably provides a pleasing hand. However, while added strength is needed, it is important not to substantially degrade the retractive force properties of the film and corresponding laminate. In this regard, the fabric can be selected so as to also be highly drapable and/or have a low bending modulus.

Fabrics suitable for use in the present invention include, but are not limited to, woven or knitted fabrics as well as nonwoven fabrics such as those made by meltblowing, spunbonding, air-laying, carding, and/or hydroentangling processes. Examples of suitable fabrics and methods of making the same include, but are not limited to, those described in U.S. Pat. No. 4,548,856 to Ali Kahn et al., U.S. Pat. No. 5,492,751 to Butt et al., U.S. Pat. No. 6,224,977 Kobylivker et al., U.S. Pat. No. 8,603,281 to Welch et al., WO99/32699 to Stokes et al., and WO16/080960 to Kupelian et al. Generally speaking, in order to limit the negative impact on the retractive force, in many embodiments it will be advantageous to utilize relatively lower basis weight fabrics. In this regard, the fabrics desirable have a basis weight less than about 30 $g/m^2$. In certain embodiments, the fabrics can have a basis weight less than about 25 $g/m^2$, 20 $g/m^2$, 18 $g/m^2$ or even 16 $g/m^2$ and further, in certain embodiments, can have a basis weight in excess of about 5 $g/m^2$, 7 $g/m^2$ or even 8 $g/m^2$. Polymers suitable for use in the nonwovens are not believed particularly limited an include polyolefins, polyesters, polyamides and so forth. In certain embodiments, the polymeric portion of the fibers can comprise at least 50%, 60%, 70%, 80% or 100% of a propylene polymer or ethylene polymer. In addition, as is known in the art, the fibers can comprise continuous or staple length fibers and still further may comprise multicomponent or multiconstituent fibers.

Further, in order to achieve still greater drapability, the fabric is desirably treated in one or more additional respects such as by the use of internal softening agents, external softening agents and/or mechanical softening treatments. By way of example, mechanical treatment of a web may be carried out by a number of different methods such as micro-creping, cold embossing, breaker bar treatment, neck stretching, and combinations thereof. However, still other methods known in the art may also be used. Examples of various methods of mechanically treating fabrics to impart improved drape or softness include, but are not limited to, those described in, U.S. Pat. No. 5,413,811 Fitting et al., U.S. Pat. No. 5,770,531 to Sudduth et al., U.S. Pat. No. 5,810,954 Jacobs et al., U.S. Pat. No. 6,197,404 Varona, U.S. Pat. No. 6,372,172 Sudduth et al. and US2004005457 to DeLucia et al. Examples of softeners include, but are not limited to, the following: olefin waxes such as a polyethylene wax; fatty acids such as erucic, oleic, stearic; fatty acid amides such as stearylamine or oleylamine; sulfated oils such as castor, olive and soybean; sulfated fatty alcohols or fatty acid esters; glycols and derivatives thereof such as glycerin, glyceryl monostearate, glycerol trioleate; polyglycol esters of fatty acids such as palmitic and stearic acids long chain amides; sugar alcohols and derivatives thereof such as sorbitol and sorbitan stearate; imidazolines; and so forth. Examples of additives for improving drape and/or hand-feel of nonwoven webs include, but are not limited to, those described in U.S. Pat. No. 5,770,531 to Sudduth et al., U.S. Pat. No. 6,197,404 Varona, US2004005457 DeLucia et al., and WO2014/044235 to Klaska et al. Increased drape and softness of the nonwoven webs can be achieved by incorporating less than about 5 percent by weight of one or more softening agents in the final composition from which the fibers or nonwoven are extruded or otherwise formed.

The elastic laminates of the present invention may be readily incorporated into an end product as is known in the art. One skilled in the art will appreciate that the elastic laminates of the present invention can be used in absorbent personal care articles including, for example, diapers, adult incontinence garments, incontinence pads/liners, sanitary napkins, panty-liners and so forth. In this regard, absorbent personal care articles commonly include a liquid-impervious outer cover, a liquid permeable topsheet positioned in facing relation to the outer cover, and an absorbent core between the outer cover and topsheet. Further, absorbent personal care articles also commonly include one or more fit related components such as fastening tapes or tabs, waistbands, elastic waist panels, elastic side panels, elasticated leg cuffs, and so forth. The unique elastic laminates made and provided herein are well suited for use as or as a component of absorbent personal care articles having one or more elasticated components. By way of example only, various personal care absorbent articles including elastic components and methods of making the same are described in U.S. Pat. No. 4,685,916 to Enloe, U.S. Pat. No. 4,816,094 Pomplum et al., U.S. Pat. No. 4,857,067 to Wood et al., U.S. Pat. No. 6,336,922 VanGompel et al., U.S. Pat. No. 6,953,452 Popp et al., U.S. Pat. No. 7,018,369 VanGompel et al., U.S. Pat. No. 7,150,731 Cazzato et al., the contents of which are incorporated herein by reference to the extent consistent herewith.

As previously noted, absorbent personal care articles generally include a liquid permeable topsheet, which faces the wearer, and a liquid-impermeable backsheet or outer cover. Disposed between the topsheet and outer cover is an absorbent core. In this regard, the topsheet and outer cover are often joined and/or sealed to encase the absorbent core. Although certain aspects of the present invention are described in the context of a particular personal care absorbent article, it will be readily appreciated that similar uses in other types of personal care absorbent articles and/or further combinations or alterations of the specific configurations discussed below may be made by one skilled in the art without departing from the spirit and scope of the present invention.

Figure 7:
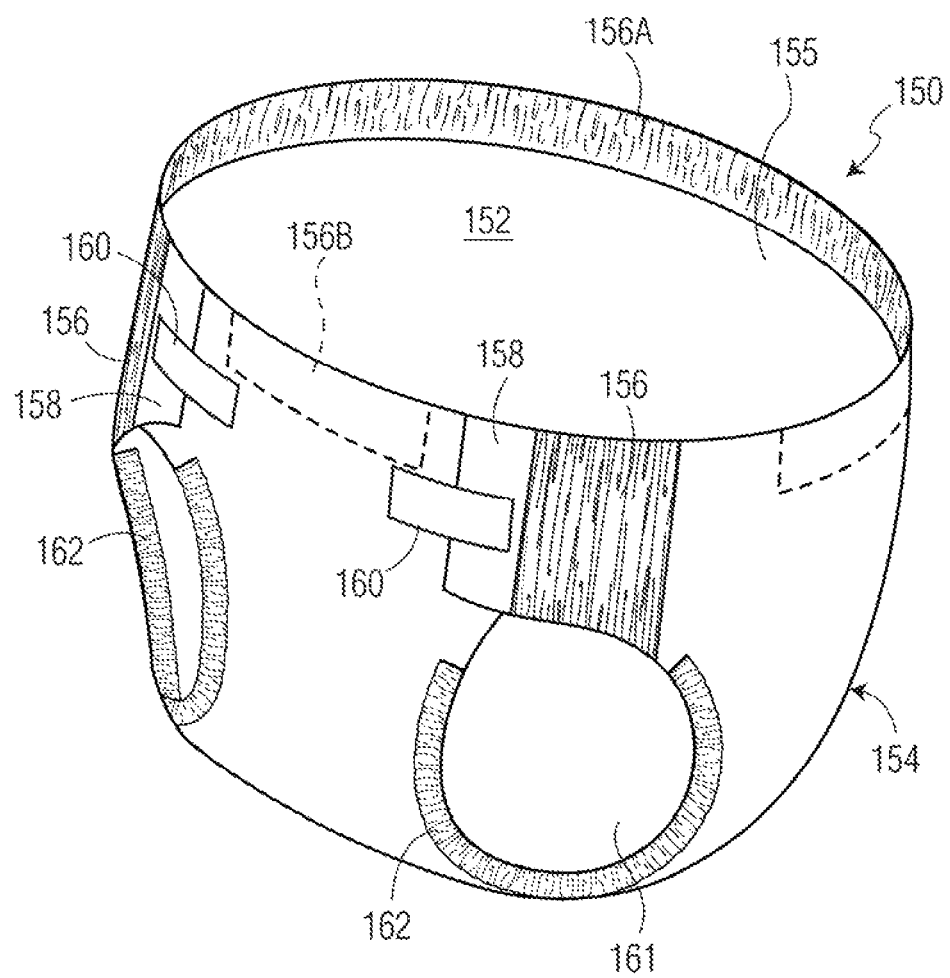
FIG. 7 is a perspective view of an absorbent personal care article incorporating composite elastic laminates of the present invention.

In a particular embodiment, and in reference to FIG. 7, a diaper 150 can comprise a liquid-impervious outer cover 154, a liquid permeable topsheet 152 positioned in facing relation to the outer cover 154, and an absorbent core (not shown) between the outer cover 154 and topsheet 152. The diaper 150 may be of various shapes such as, for example, an overall rectangular shape, T-shape, hourglass shape and so forth. The topsheet is generally coextensive with the outer cover but may optionally cover an area that is larger or smaller than the area of the outer cover, as desired. While not shown, it is to be understood that portions of the diaper, such as a marginal section of the outer cover, may extend past and around the terminal edges of the product and form a portion of the body-facing layer.

The topsheet or body-side liner 152 desirably presents a body facing surface which is compliant, soft to the touch, and non-irritating to the wearer's skin. The topsheet 152 is desirably employed to help isolate the wearer's skin from liquids held in the absorbent core. Topsheets are well known in the art and may comprise a wide variety of materials, such as porous foams, reticulated foams, apertured plastic films, natural fibers (wool, cotton fibers, etc.), synthetic fibers (polyester, polypropylene, polyethylene, etc.), combinations of natural and synthetic fibers, and so forth. Topsheets can comprise a single layer or a multiple layers including a combination of one or more different materials. Apertured films, nonwoven fabrics, and laminates thereof, are commonly utilized to form topsheets.

Suitable topsheet materials include, but not limited to, those described in U.S. Pat. No. 5,382,400 to Pike et al., U.S. Pat. No. 5,415,640 to Kirby et al., U.S. Pat. No. 5,527,300 to Sauer, U.S. Pat. No. 5,994,615 to Dodge et al., U.S. Pat. No. 6,383,960 to Everett et al., U.S. Pat. No. 6,410,823 to Daley et al., and US2014/0121623 to Biggs et al.

The backsheet or outer cover 154 comprises a liquid-impervious material. Desirably, the outer cover comprises a material that prevents the passage of water but allows air and water-vapor to pass there through. The outer cover can comprise a single layer of material or multiple layers including one or more layers of different materials. In a particular embodiment, the outer cover can comprise a film fixedly attached or bonded to one or more nonwoven webs. The particular structure and composition of the outer cover may be selected from various combinations of films and/or fabrics. In this regard, the outer most layers are generally selected to provide the desired strength, abrasion resistance, tactile properties and/or aesthetics. Suitable outer covers include, but are not limited to, those described in U.S. Pat. No. 4,041,203 to Brock et al., U.S. Pat. No. 6,075,179 et al. to McCormack et al., U.S. Pat. No. 6,111,163 to McCormack s et al., and US2015/099086 to Cho et al., the contents of which are incorporated herein to the extent consistent herewith.

In the present embodiment, the diaper 150 may include an elastic waistband 156 located about the waist opening 155. The elastic composite providing the elasticity for the waistband can be located either exposed on the skin-contacting side of the topsheet, exposed on the outside of the backsheet and/or positioned between the topsheet and backsheet. When positioned on the skin-contacting surface of the topsheet, the waistband can also provide a dual function of acting as a containment pocket as is known in the art. Further, in certain embodiments the diaper may be provided with separate front and rear waistbands respectively 156A, 156B. Alternatively, for certain pant style garments, a continuous elastic waistband may be employed.

The diaper 150 may, in certain embodiments, further include elastic side panels 157. The elastic laminate providing the elasticity to the side panels can form all or a portion of each side panel. For example, optionally, an inelastic panel 158 may be positioned between the fastener 160 and the elastic laminate forming a portion of the side panel 156. As is known in the art, the elastic side panels may be integrally formed with the backsheet and/or topsheet or, alternatively, comprise a separate component that is attached to the central diaper chassis such as being attached to one or more of the backsheet and/or topsheet.

The diaper 50 may further include elastic leg cuffs 162 located about the leg openings 161. The leg cuffs may be curved about the leg opening or multiple leg elastics may be used extending proximate the leg openings towards the side panels and front and rear waist openings.

The personal care articles can, optionally, contain one or more additional elements or components. In this regard, numerous additional features and various constructions are known in the art. One skilled in the art will appreciate the application and use of the elastic composite of the present invention may be used as or in one or more components to provide the desired elasticity and hand-feel. In addition, one skilled in the art will appreciate that the elastic laminate may similarly be used to provide elasticity and/or fit enhancing attributes to other garments or articles including for example protection garments. In this regard, the elastic composite can be employed to form elastic panels, waistbands, cuffs, fastening tabs and so forth. By way of example only, the elastic composite may be employed in the garments as described in U.S. Pat. No. 5,594,955 Sommers, U.S. Pat. No. 6,799,331 Griesbach et al., and US2005/097659 to Aroch et al., the contents of which are incorporated herein by reference to the extent consistent herewith. In a similar manner, the elastic composite may be employed in still other articles such as sweat pads, bandages, body-wraps, and protection articles.

In a further aspect, the elastic composite laminate of the present invention may be used as a wiper suitable for personal use or use on hard surfaces. The selection of the individual layers will of course vary with respect to the intended end use. For example, for use as a personal care wipe, typically the materials selected will have a greater emphasis on softness and hand-feel whereas those intended for hard surface cleaning may have a greater emphasis on strength and durability. The laminates of the present invention may be used for the formation of wipes, stacks of wipes and other products including, but not limited to, those described in U.S. Pat. No. 3,401,927 to Frick et al.; U.S. Pat. No. 4,171,047 to Doyle et al., U.S. Pat. No. 4,502,675 to Clark et al.; U.S. Pat. No. 4,353,480 to McFadyen, U.S. Pat. No. 4,651,895 Niske et al., U.S. Pat. No. 4,741,944 to Jackson et al., U.S. Pat. No. 4,778,048 to Kaspar et al., U.S. Pat. No. 5,264,265 to Kaufmann, U.S. Pat. No. 5,310,398 to Yoneyama, U.S. Pat. No. 5,964,351 Zander, U.S. Pat. No. 6,158,614 to Haines et al., U.S. Pat. No. 6,592,004 to Huang et al. and U.S. Pat. No. 6,612,462 to Sosalla et al.

Test Methods

Tensile Strength: As used herein "tensile strength" or "strip tensile", is the peak load value, i.e. the maximum force produced by a specimen, when it is pulled to rupture. Samples for tensile strength testing are prepared by die cutting test specimens to a width of 25 mm and length of approximately 152 mm. The instrument used for measuring tensile strengths is an MTS Criterian 42 and MTS TestWorks™ for Windows Ver. 4 (MTS Systems Corp., Research Triangle Park, NC). The load cell is selected, depending on the strength of the sample being tested, such that the peak load values fall between 10 and 90 percent of the load cell's full scale load. The gauge length is 76 mm and jaw length is 76 mm. The crosshead speed is 305 mm/minute, and the break sensitivity is set at 70% and the slope preset points at 70 and 157 g. The sample is placed in the jaws of the instrument and centered with the longer dimension parallel to the direction of the load application. The test is then started and ends when the specimen breaks. The peak load is determined, for purposes herein, based upon the CD tensile strength. Six (6) representative specimens are tested, and the arithmetic average of all individual specimen tested is the tensile strength for the product.

Extension at 2000 gf: This value is the percent extension of the elastic laminate in the machined direction with a stretching force of 2000 gf applied thereto. Samples for tensile strength testing are prepared by die cutting test specimens to a CD length of 25 mm and an MD length of approximately 152 mm. The instrument used for measuring tensile strengths is an MTS Criterian 42 and MTS TestWorks™ for Windows Ver. 4 (MTS Systems Corp., Research Triangle Park, NC). The load cell is selected, depending on the strength of the sample being tested, such that the peak load values fall between 10 and 90 percent of the load cell's full scale load. The gauge length is 50 mm and the rubber faced grips are 25×102 mm. The crosshead speed is 500 mm/minute. The sample is placed in the jaws of the instrument and centered with the longer dimension parallel to the direction of the load application. The test is then started and is initially elongated to stop, returning the sample to the initial gauge length and then pulling the sample to break. Stress/strain data indicate the force required to elongate the specimen. The load at elongation output characterizes the force at the specified point of specimen elongation. The higher the force value, the more difficult it is to elongate the specimen. The determination of the load at the desired elongation is taken from the second cycle. Six (6) representative specimens are tested, and the arithmetic average of all individual specimen tested is the tensile strength for the product.

Tensile Strength: As used herein "tensile strength" or "strip tensile", is the peak load value, i.e. the maximum force produced by a specimen, when it is pulled to rupture. Samples for tensile strength testing are prepared by drying and then die cutting test specimens to a width of 25 mm and length of approximately 152 mm. The instrument used for measuring tensile strengths is an MTS Criterian 42 and MTS TestWorks™ for Windows Ver. 4 (MTS Systems Corp., Research Triangle Park, NC). The load cell is selected, depending on the strength of the sample being tested, such that the peak load values fall between 10 and 90 percent of the load cell's full scale load. The gauge length is 76 mm and jaw length is 76 mm. The crosshead speed is 305 mm/minute, and the break sensitivity is set at 70% and the slope preset points at 70 and 157 g. The sample is placed in the jaws of the instrument and centered with the longer dimension parallel to the direction of the load application. The test is then started and ends when the specimen breaks. The peak load is determined, for purposes herein, based upon the CD tensile strength. Six (6) representative specimens are tested, and the arithmetic average of all individual specimen tested is the tensile strength for the product.

As used herein "basis weight" is determined using the average dry weight of twelve (12) 150 mm×150 mm specimens.

As used herein "caliper" or "thickness" of a sheet is determined by using a micrometer having an acrylic platen with a pressure foot area of 45.6 $cm^2$ (3 inch diameter), providing a load of 0.345 kPa (0.5 psi), and the reading is taken after a dwell time of 3 seconds. A sample is cut having a size of 90×102 mm (3.5×4 inches) is used for the measurement.

As used herein air permeability is conducted on dry samples and determined using a TEXTEST FX 3300 Air Permeability Tester from Textest AG using a test pressure of 125 Pa and a test head area of 38 $cm^2$.

EXAMPLE

The elastic film for this example comprised a blend of 20% by weight propylene-based elastomer (Vistamaxx™ 6102 from ExxonMobil) and 80% by weight styrenic block copolymer elastomer (Kraton™ 6673 from Kraton Corporation). The outer facing materials utilized were 10 $g/m^2$ polypropylene spunbond fiber nonwoven webs.

The elastic film was formed by casting onto a chill roll operating at 4 M/minute. The elastic form was directed from the chill roll to an S-wrap roller assembly operating at a speed of approximately 6 M/minute. From the S-wrap roller assembly, the film was directed to a pair of inter-meshing grooved rolls operating at a speed of approximately 23 M/minute and that were heated to a temperature of approximately 85° C. The grooved rollers each had 3.14 ridges per cm (8 ridges per inch) with a tip-to-tip distance of 0.3175 cm (0.125 in.) and a rounded tip with a radius of 0.038 cm (0.015 in.). The degree of engagement, i.e. the depth that the ridges extended into the opposed grooves of the opposite roller, was 0.32 cm (0.126 in.).

The outer facing layers were simultaneously unwound from winding rolls and directed into the nip of the grooved rollers so as to lay adjacent opposite sides of the elastic film forming a nonwoven/film/nonwoven stack. The nonwoven facings were unwound and directed into the nip of the grooved roll at substantially the same speed as the grooved rolls. The three layers were stretched in the cross-direction and bonded to one another to form a cohesive laminate as a result of passing through the nip of the grooved roll assembly. After exiting the grooved roll assembly, the laminate was allowed to retract and would onto a winder roll operating at a speed of 9.1 M/min. The resulting laminate had a basis weight of 71 g/m², with the film having a basis weight of about 19 g/m² and the two outer facings having a combined basis weight of about 53 g/m². The laminate has a first cycle load at 50% elongation of 297 g/f. Also, the laminate has percent stretch at 2000 g/f of 116%.

Figure 8:
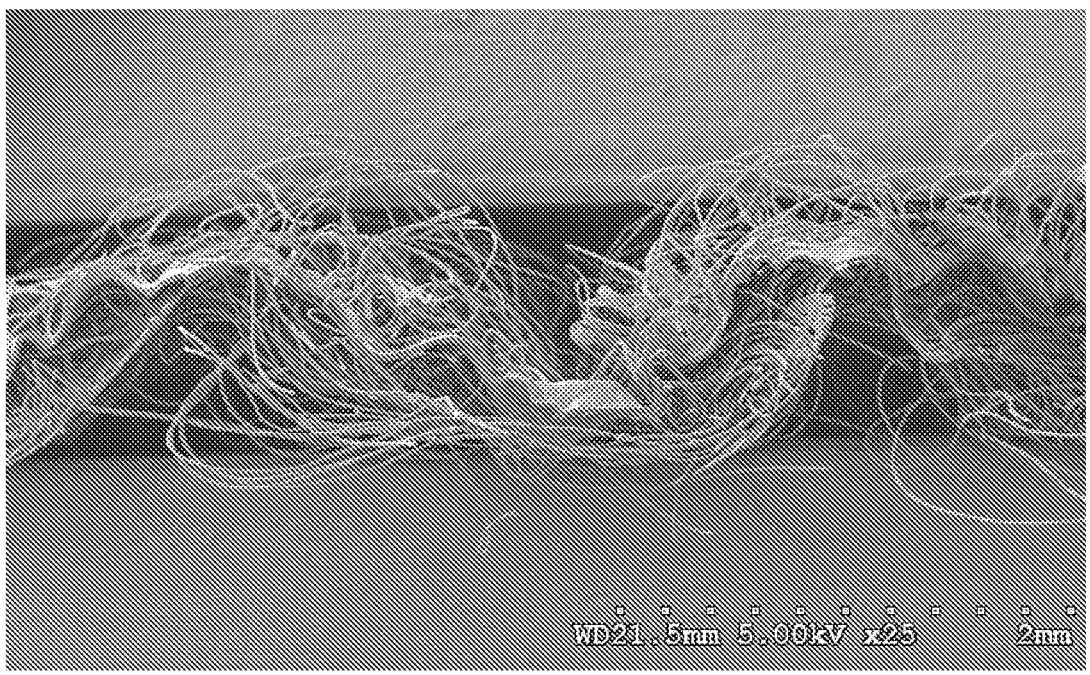
FIG. 8 is a CD cross-sectional view of a laminate of the present invention.
Figure 9:
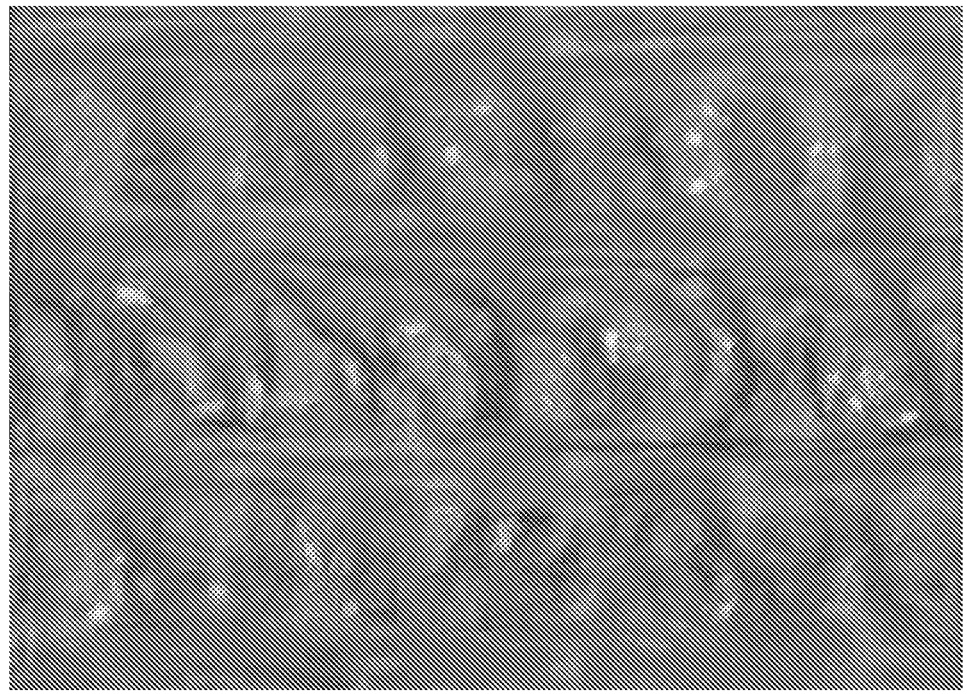
FIGS. 9 and 10 are photographs of a top down view of an elastomeric laminate of the present invention with the proximate outer facing layer removed to expose the elastic layer and underlying nonwoven web.
Figure 10:
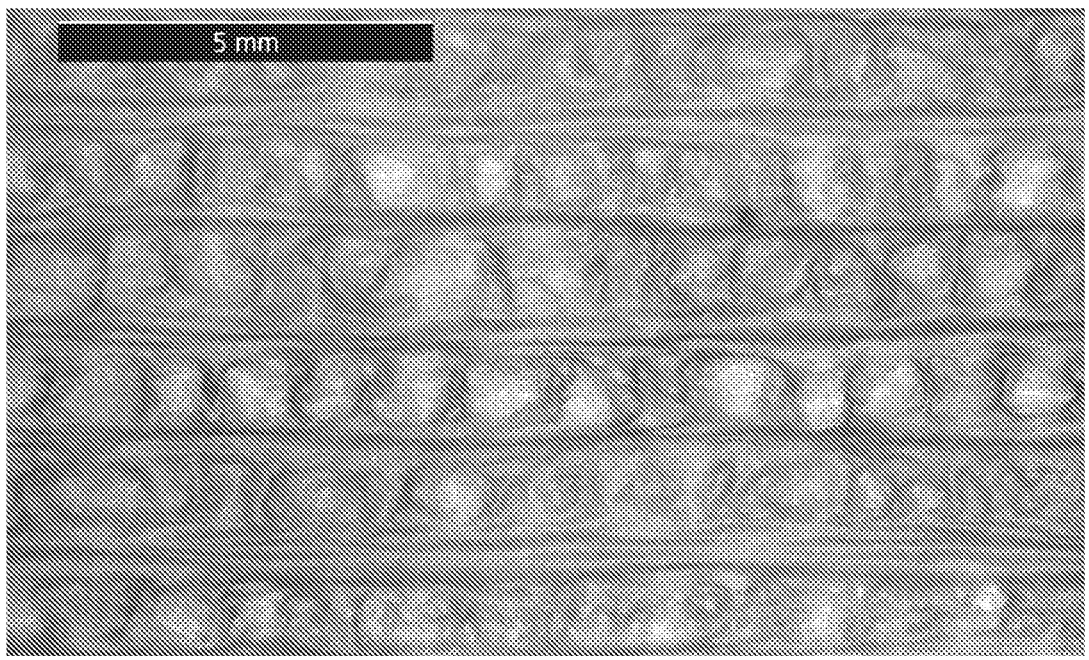
Figure 11:
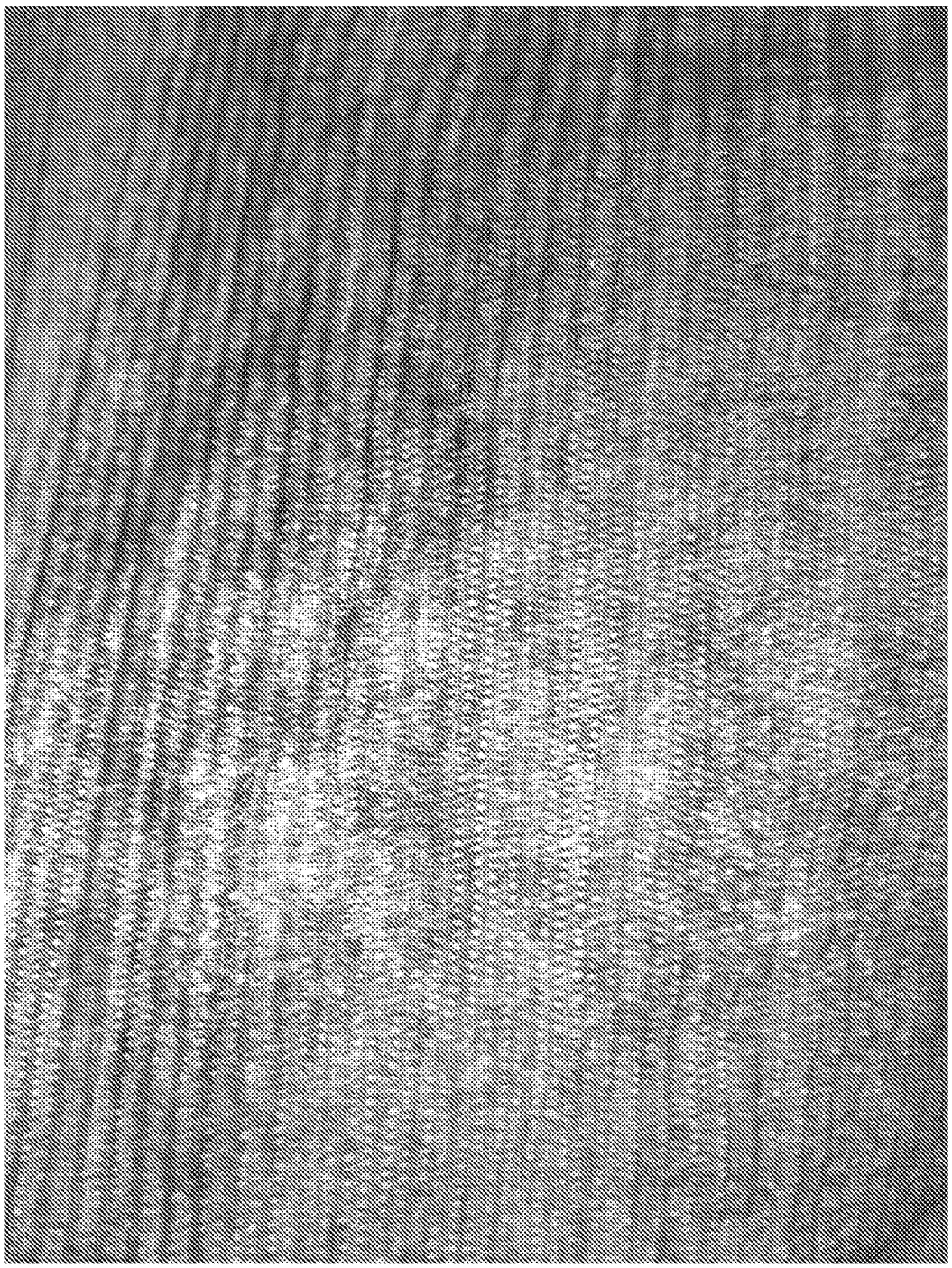
FIG. 11 is a rear-lit photograph of a 3-layer laminate of the present invention.

The resulting laminate is shown in FIGS. 8-13. As best seen in FIGS. 8-9, the elastic film extends across the laminate in the cross-direction. However, as best seen in reference to FIGS. 9 and 10, the elastic film has distinct segments that alternate in the cross-direction and extend continuously in the machine direction. The alternating segments include apertured and unapertured segments. The unapertured segments of this example include micro-gathers that extend along and are substantially aligned with the machine direction. Interposed between the unapertured segments are the aperture segments. The apertured strips are strewn with numerous small apertures extending through the entirety of the film. Further, as best seen in reference to FIG. 10, the elastic film along the aperture segments also have a series of puckers with furrows that are substantially aligned with the cross-direction. The apertures are located predominantly between the puckers and results in the laminate having a greater degree of opacity in these areas. As seen in FIGS. 10 and 11, the areas between the puckers are less opaque and in addition to the apertures are believed to have been thinned to a significantly greater extent than the other areas of the film.

Figure 12:
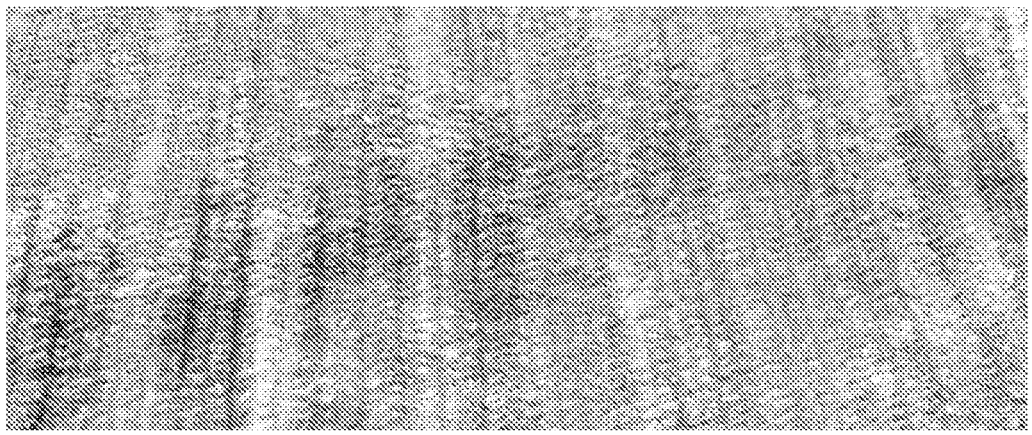
FIGS. 12 and 13 are photographs of a perspective view of a 3-layer elastic laminate of the present invention.
Figure 13:

In addition, as best seen in FIGS. 12 and 13, the resulting laminate presents a corduroy appearance. The laminate has a series of alternating furrows that extend in the machine direction; the furrows being defined by alternating relatively thicker and thinner portions. In addition, the outer nonwoven webs of the elastic laminate include a multitude of gathers that extend over both the relatively thicker and thinner regions as well as over the first and second segments.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A composite elastic material comprising:
    a laminate having a first fabric attached to an elastic film, the laminate extends in a first direction and a second direction perpendicular to the first direction;
    the first fabric is extensible in the first direction and the laminate is elastic in the first direction; and
    wherein the laminate is formed by inserting the first fabric and the film in a stacked relationship and stretched in the first direction into intermeshing grooved rolls, such that the first fabric and film become bonded and stretched in the second direction providing controlled rupturing of the film resulting in:
    the film having a plurality of alternating first and second segments that extend continuously in the first direction, the first segments of the elastic film being strewn with randomly positioned apertures of irregular size and shape,
    the second segments of the elastic film being substantially devoid of apertures; and
    wherein the laminate has an air permeability of between about 150-1000 CFM.

2. The composite elastic material of claim 1 wherein the laminate has between 0.5 and 14 first segments per cm along the second direction and further wherein the laminate has between 0.5 and 14 second segments per cm along the second direction.

3. The composite elastic material of claim 1 wherein the laminate has between 1 and 12 first segments per cm along the second direction and further wherein the laminate has between 1 and 12 second segments per cm along the second direction.

4. The composite elastic laminate of claim 1 wherein the fabric comprises a nonwoven web of olefin polymer fibers and further wherein the elastic film comprises an olefin elastomer.

5. The composite elastic laminate of claim 1 wherein the first fabric has gathers extending across said first and second segments.

6. The composite elastic laminate of claim 1 wherein the first and second segments comprise a width in the second direction between about 2 mm and 20 mm.

7. The composite elastic laminate of claim 1 wherein the elastic laminate has a percent extension of between about 75% and about 260% at an extension force of 2000 g-f.

8. The composite elastic laminate of claim 1 wherein the elastic film extends continuously across at least about 75% of the length of the laminate in the second direction.

9. The composite elastic laminate of claim 1 wherein the first segments extend continuously along the length of the laminate in the first direction and further wherein the second segments extend continuously along at least about 80% of the length of the laminate in the first direction.

10. The composite elastic laminate of claim 1 wherein the first fabric comprises a nonwoven web and further wherein the film is bonded to the fibers of the first nonwoven web.

11. The composite elastic laminate of claim 10 further comprising a second fabric comprising a nonwoven web and wherein the film is position between the first and second fabrics.

12. The composite elastic laminate of claim 11 wherein the first and second fabrics have gathers extending across the first and second regions of the film and further wherein the film is bonded to both the first and second fabrics.

13. The composite elastic laminate of claim 11 wherein the laminate has a basis weight less than about 60 g/m² and wherein the elastic film comprises between about 10 to about 40% of the basis weight of the laminate and still further wherein the laminate has a percent stretch of between about 80% and 250% at 2000 g-f.

14. The composite elastic laminate of claim 13 wherein the elastic film predominantly comprises an elastomer selected from the group of ethylene polymers, propylene polymers and styrenic block copolymers.

15. The composite elastic laminate of claim 1 wherein the laminate has a basis weight, in an untensioned state, of between about 15 and about 60 g/m² and further wherein the film comprises between about 10% and about 40% by weight of the laminate.

16. The composite elastic laminate of claim 14 wherein the laminate has a percent stretch of between about 80% and 260% at 2000 g-f.

17. The composite elastic laminate of claim 1 wherein the film predominantly comprises an olefin elastomer and the first nonwoven web comprises fibers predominantly comprising a first olefin polymer and further wherein the Vicat softening point of the film is lower than the Vicat softening point of the fibers.

18. The composite elastic laminate of claim 1 wherein the first segments of the film have a plurality of micro-furrows substantially aligned with the first direction.

19. The composite elastic laminate of claim 1 wherein the laminate is elastic in the first direction and inelastic in the second direction.

20. The composite elastic laminate of claim 1 wherein the second segments of the film have a plurality of puckers that are substantially aligned with the second direction.

* * * * *